United States Patent
Constabel et al.

(10) Patent No.: US 7,868,226 B2
(45) Date of Patent: Jan. 11, 2011

(54) POPLAR TRANSCRIPTION FACTORS

(75) Inventors: C. Peter Constabel, Victoria (CA); Robin D. Mellway, Victoria (CA)

(73) Assignee: University of Victoria Innovation and Development Corporation, Victoria, BC (CA)

( * ) Notice: Subject to any disclaimer, the term of this patent is extended or adjusted under 35 U.S.C. 154(b) by 0 days.

(21) Appl. No.: 12/626,844

(22) Filed: Nov. 27, 2009

(65) Prior Publication Data

US 2010/0074995 A1   Mar. 25, 2010

Related U.S. Application Data

(62) Division of application No. 12/341,715, filed on Dec. 22, 2008, now Pat. No. 7,714,192.

(30) Foreign Application Priority Data

Dec. 21, 2007   (CA) .................................... 2612655

(51) Int. Cl.
*A01H 5/00*        (2006.01)
*C12N 15/82*       (2006.01)
*C12N 5/14*        (2006.01)
*C07H 21/00*       (2006.01)

(52) U.S. Cl. ...................... 800/295; 800/278; 800/320; 435/419; 435/468; 536/23.6

(58) Field of Classification Search ....................... None
See application file for complete search history.

(56) References Cited

PUBLICATIONS

Tuskan et al., NCBI, GenBank, Sequence Accession No. CM000342, Published Oct. 11, 2006.*
In et al., NCBI, GenBank, Sequence Accession No. CF936298, published Nov. 15, 2004.

* cited by examiner

*Primary Examiner*—Vinod Kumar
(74) *Attorney, Agent, or Firm*—Klarquist Sparkman, LLP

(57) ABSTRACT

A nucleic acid molecule comprising a nucleotide sequence selected from the group consisting of nucleotide sequences set forth in SEQ ID NO:1-6 and 11, particularly SEQ ID NO: 3. The nucleotide sequence encodes at least a corresponding amino acid sequence set forth in SEQ ID NO: 12-17 and 26. The nucleic acid sequences and corresponding amino acid sequences regulate the flavonoid pathway, and more particularly they regulate the proanthocynanidin biosynthetic pathway and proanthocynanidin biosynthesis in a plant. One embodiment relates to methods of producing transformed plants comprising introducing into a cell of a plant a nucleic acid sequence selected from the group consisting of SEQ ID NO:1-6 and 11, particularly SEQ ID NO: 3 and regenerating a transformed plant from the transformed cell. Another embodiment relates to a host plant cell comprising at least one of the nucleic acid sequences set forth in SEQ ID NO:1-6 and 11.

15 Claims, 26 Drawing Sheets

SEQ ID NO:1     Isolated nucleic acid sequence of *MYB183* cggccgttgagcttttgaggaatatagagggagaatagagagaggatgggtagaagttcaaaagggggggctaattcga
ggaacttggactgctactgaagacaaaattcttacagcatatgttagaaaatatggtgaagggaactgggctagggttac
aagggaaacaggtctgaagagatgtggcaagagttgcaggcttcgttggctgaattatctaaaaccagatgttaaaaga
ggaaacattagcccagatgaagaagatctcattattaggcttcacaagctcttaggcaacagatgggctttaatagctgga
aggcttccaggtcggacggacaatgagatcaagaattactggaattcaaccttgaaaagaaaggtacaagctaacgatc
aaaaacagcctagaagagggaataaagacacaaaaaaacaaaccagaaagacctcaacaggattgaatatggcggc
accatgcacaaacagtagtcttccttcaccaccagtcttagctgaaaatatagagactgatcagatcctcacagcatcctc
cattgaagaaggaaccttggaaaaatatctgatagaaaatcccaactcaaatgatgagctcttgctatttactaacgataat
gatgtgccttgcaacttcttgatggatcttgatatggggcagatgagcttctctgattttctccaaactgatatcttctcagata
gcaataacatgcttgttaatgggcctgcaccttcttatccagatgaagcttctttgttccccgagaatatgctgcagaattgg
atgtgtgaggatggctttgaacttgaactggctatgggtccttgatcaacgatcactgctttcgttcttgtcaattcaaggcg
attaataagcatgtcttctgcttcttcttcttcttctccttcttcttcttcttcttatcattatcctttcttgttccaggttattgagatta
aataaggggagcagagttcgctcatatattccctttgcctgtttccattttctcagcatttgaacataagaattccaattagaa
ccgcggtaagttggatggtccctgtatggaagaaacggcatgcttttaattggaacacaaatatccaatct

FIG. 11

SEQ ID NO:2        Isolated nucleic acid sequence of *MYB086* atgggaaggagtccatgttgctccaaggaaggactcaacaggggagcctggactgccttggaagacaaaatactgatg gcttatattaaagcccatggagaaggcaactggagaaacctccccgagagagcaggtttgaagagatgtggaaagagct gtagactcagatggttaaattatcttagaccagacatcaagagaggcaacatttcccatgatgaagaagaactcattatcag gctccataaccttcttggtaacagatggtccctaatagctggaaggctacctgggcgaacagacaatgaaatcaagaatta ttggaacactactctggggaaaaaagctaaaggccaatcatcttcacaatccaaacaaagctctcaaagaaaatctagag caattaaacccatgaccagcacccaaccatcaaagtcaacacagacaacccaagtaatccgcaccaaggccactaggt gcaccaaggttttgctctcattacagtcaccaccaccgacactgacaccactaccaccacctgaaattctctcctcaacagc catgaacgacccctctcaagcttccttgataaatcatcaacaagatggtccaaattttcattgcggaactgaagaggttcatg catgtcatgatggctcagatttcttcaatttcgggaagtggaatgaaattcaaccaaatgatatagacggagacacactaat gaagagtggttgtaaccggaatttgtccaggggttctgaatattccttgggcttatttgatgacctcatgttcaaggactggg cactgaatcattgtcctgaagacaatgcaactttggacctagagtctctcgcacatttgcttgattctgaagagtggcc

FIG. 12

SEQ ID NO:3        Isolated nucleic acid sequence of *MYB134* atggggaggagtccatgttgctccaaggaggggctcaacagaggagcctggactgccttagaagacaaaatactgacg
gcgtatatcaaggcccacggagaaggcaaatggagaaacctccccaagagagcaggtttgaagagatgtggcaagag
ctgtagactcagatggttaaattatcttagaccggacatcaagagaggcaacatttccaatgatgaagaagaactcattgtc
aggctccataagcttcttggtaacagatggtctttaatagctggaaggctacctgggcgaacagacaatgaaatcaagaac
tactggaacactactctggggaagaaagcaactgctcaagcatctccacagtccaaacaaaattcccagagctttaaaaa
acgagcaattgaacccatgactaacacccaatcatcaaagtcaacactggcaacccaagtaatccccaccaaggccact
aggtgcactaaggttttcctctcattacagtcaccaccaccaccaataccgccacctaaaactctctcctcaacagccatag
acgacccaccacaagctcccttgttaaatcatcaacaagatagcccaaatcttcactgtcgtgatgatgactcagatttcttg
aattttggacactggaatgagtttcaaccgagtgatggaggtacactaattgacaatgattgtgacaagaatctgtccattga
ttcttaccattccttagccgtatctgatgacctaatgttcaaggattgggccctgaatcgttgtctcgatgacaattcaactttg
gacttggaatctttggcacatttgcttgactctgaagagtggcctgagatgcgacattga

FIG. 13

SEQ ID NO:4   Isolated nucleic acid sequence of *MYB097* gtaccaagtatccagtcatccagaggacatcgagtagctagtagtgagatacagcaagagatgggaagaaagccgagg
tgctcagcggatggtatgaacaaaggagcatggacacctcttgaagatgaaatgcttgtggattatgtcaagatscatggt
gaaggtaaatggagcaatattgtcaaagaaacaggacttaagagatgtgggaagagttgcaggcttcgctggatgaatta
tctgagacctgatattaagagaggcaacatctcagatgatgaagaagacctcattatcaggctgcataagctcttaggcaa
cagatggtctctgatagcaggacggcttccgggacgaacagataacgaaataaagaattattggcacaccaatatcgcta
agaaggcacaacattcgcaatctcggaagcagcctrgagttgataggaaacaaatagcatcaggatctgaaaatggggc
arcagcatcaaatktcaagaatcagaccattgaatcacagtactgcactactggggtggttgttcccwctactgcattacaa
gaaaacaatatggctcaagatcatctagttagtactcttgcaatggcaccatccaacacacatcatgaaaatgaatcatcaa
gcaaggggttagcatctggggataatgacaatttgtccaacattttgatggattttcattatatggaagacttctwcaagattc
ttgattcagacttcccaaagttaagtgacctcaatgatataactagtactgctaatcattccamtaataccatacaggtagat
ggtgatcattatagtgtgtctattaatggatgcaatccaagagaaatagcagggttttctgaattgttggaggcagattggac
tagcaataaatgcgttcaagctgaacaaggttttgatttcatgtcattgctttcatttcttgatttaaccgatgagtaatggacag
aagatgccttagccaataatctacgtcaagttgctttcatgtccacgccttccaggctaatagttctcgagtttgaacctctctc
atgttaaaaaaaaaaaaaaaaaaaaaaaa

FIG. 14

SEQ ID NO:5        Isolated nucleic acid sequence of *MYB087* agagatgggaaggagtccatgttgctccaaggaaggactcaacaggggagcctggactgccttggaagacaaaacact
gatggcttatattaaagcccatggagaaagcaactggagaaacctccccgagagagcaggtttgaagagatgtggtaag
agctgtagactcagatggttaaattatcttagaccagacatcaagagaggcaacatttcccatgatgaagaagaactcatta
tcaggctccataaccttcttggtaacagatggtccgtaatagctggaaggctacctgggcggacagacaatgaaatcaag
aattattggaacactactctggggaaaaaagctaaaggcgaatcatcttcacaatccaaacaaagctgtcaaagcaaatct
agagcaattaaacccatgaccagcacccaaccatcaaagtcaacacagacaacccaagtaatccgcatcaaggccact
aggtgcaccaaggttttgctctcattacagtcaccaccaccgacacggacaccactaccaccacctgaaattctctcctca
acagccatgaacgacccctctcaagcttccttgataaatcatcaacaagatggtccaaattttcattgcggaactgaagagg
ttcatgcatgtcatgatggctcagatttcttcaatttcgggaagtggaatgaaattcaaccaaatgatatagacggagataca
ctaatgaagagtggttgtaaccggaatttgtccaggggttctgaatgttccttgggcatatttgatgacctcatgttcaaggac
tgggcactgaatcattgtcctgaagacaatgcaactttggacctagagtctctcgcacatttgcttgattctgaagagtggcc
atgagattagacactgacgagaaactacagcaaaatctccaccctagaagatatattggcacttgtggcatatctcaattga
ttattattcgtagaaatcaaagtaataattagcttgtgtatggtgtgaaattagagcaagtctgtaatgatttagcatttgt

FIG. 15

SEQ ID NO:6         Isolated nucleic acid sequence of MYB Domain atggggaggagtccatgttgctccaaggaggggctcaacagaggagcctggactgccttagaagacaaaatactgacg gcgtatatcaaggcccacggagaaggcaaatggagaaacctccccaagagagcaggtttgaagagatgyggcaaga gctgtagactcagatggttaaattatcttagaccggacatcaagagaggcaacatttccaatgatgaagaagaactcattgt caggctccataagcttcttggtaacagatggtctttaatagctggaaggctacctgggcgaacagacaatgaaatcaagaa ctactggaacactactctggggaagaaagcaactgctc

FIG. 16

SEQ ID NO:11   Isolated nucleic acid sequence of a MYB transcription factor from *P. trichocarpa* gttgtggaagtgcgcgtgtgtggtgatcgtagagagagatggggaggagtccatgttgctccaaggagggactcaacag
aggagcctggactgccttagaagacaaaatactgacggcgtatatcaaggcccacggagaaggcaaatggagaaacct
ccccaagagagcaggtttgaagagatgcggcaagagctgtagactcagatggttaaattatcttagaccggacatcaaga
gaggcaacatttccaatgatgaagaagaactcattgtcaggctccataagcttcttggaaacagatggtctttaatagctgg
aaggctacctgggcgaacagacaatgaaatcaagaactactggaacactactctggggaagaaagccactgctcaagc
atctccacagtccaaacaaaattcccagagctttaaaaaacgagcaattgaacccatgactaacacccaatcatcaaagtc
aacactggcaacccaagtaatccccaccaaggccactaggtgcactaaggttttcctctcattacagtccccaccaccacc
aatactgccacctaaaactctctcctcaacagccatagacgacccaccacaagctcccttgttaaatcatcaacaagatag
cccaaatcttcacggccatgatgactcagatttcttgaattttggacactggaatgagtttcaatcgagtgatggaggtacac
taattgacaatgattgtgacaagaatctgtccattgattcttaccattccttagccttatctgatgacctaatgttcaaggattgg
gccctgaatcgttgtctcgatgacaattcaactttggacttggaatctttggcacatttgcttgactctgaagagtggcctgag
atgcgacattgacgagaaacgacgacaaaatctccaccgtagaagatatgtatacaattgatctgcccatgaataaatagg
cattcagtgttgatgatcaccacttgtagaatgtcttaattgactattaatgtagaaatgaaagta

FIG. 17

SEQ ID NO: 12  Amino acid sequence of *MYB183*

MGRSSKGGLIRGTWTATEDKILTAYVRKYGEGNWARVTRETGLKRCGKSC
RLRWLNYLKPDVKRGNISPDEEDLIIRLHKLLGNRWALIAGRLPGRTDNEIK
NYWNSTLKRKVQANDQKQPRRGNKDTKKQTRKTSTGLNMAAPCTNSSLPS
PPVLAENIETDQILTASSIEEGTLEKYLIENPNSNDELLLFTNDNDVPCNFLMD
LDMGQMSFSDFLQTDIFSDSNNMLVNGPAPSYPDEASLFPENMLQNWMCED
GFELELAMGP

FIG. 18

SEQ ID NO: 13   Amino acid sequence of MYB086

MGRSPCCSKEGLNRGAWTALEDKILMAYIKAHGEGNWRNLPERAGLKRCG
KSCRLRWLNYLRPDIKRGNISHDEEELIIRLHNLLGNRWSLIAGRLPGRTDNE
IKNYWNTTLGKKAKGQSSSQSKQSSQRKSRAIKPMTSTQPSKSTQTTQVIRT
KATRCTKVLLSLQSPPPTLTPLPPPEILSSTAMNDPSQASLINHQQDGPNFHCG
TEEVHACHDGSDFFNFGKWNEIQPNDIDGDTLMKSGCNRNLSRGSEYSLGL
FDDLMFKDWALNHCPEDNATLDLESLAHLLDSEEWP

FIG. 19

SEQ ID NO: 14   Amino acid sequence of MYB134

MGRSPCCSKEGLNRGAWTALEDKILTAYIKAHGEGKWRNLPKRAGLKRCG
KSCRLRWLNYLRPDIKRGNISNDEEELIVRLHKLLGNRWSLIAGRLPGRTDN
EIKNYWNTTLGKKATAQASPQSKQNSQSFKKRAIEPMTNTQSSKSTLATQVI
PTKATRCTKVFLSLQSPPPPIPPPKTLSSTAIDDPPQAPLLNHQQDSPNLHCRD
DDSDFLNFGHWNEFQPSDGGTLIDNDCDKNLSIDSYHSLAVSDDLMFKDWA
LNRCLDDNSTLDLESLAHLLESEEWPEMRH

FIG. 20

SEQ ID NO: 15   Amino acid sequence of MYB097

MGRKPRCSADGMNKGAWTPLEDEMLVDYVKXHGEGKWSNIVKETGLKRC
GKSCRLRWMNYLRPDIKRGNISDDEEDLIIRLHKLLGNRWSLIAGRLPGRTD
NEIKNYWHTNIAKKAQHSQSRKQPXVDRKQIASGSENGAXASNXKNQTIES
QYCTTGVVVPXTALQENNMAQDHLVSTLAMAPSNTHHENESSSKGLASGD
NDNLSNILMDFHYMEDFXKILDSDFPKLSDLNDITSTANHSXNTIQVDGDHY
SVSINGCNPREIAGFSELLEADWTSNKCVQAEQGFDFMSLLSFLDLTDE

FIG. 21

SEQ ID NO: 16   Amino acid sequence of MYB087

MGRSPCCSKEGLNRGAWTALEDKTLMAYIKAHGESNWRNLPERAGLKRCG
KSCRLRWLNYLRPDIKRGNISHDEEELIIRLHNLLGNRWSVIAGRLPGRTDNE
IKNYWNTTLGKKAKGESSSQSKQSCQSKSRAIKPMTSTQPSKSTQTTQVIRIK
ATRCTKVLLSLQSPPPTRTPLPPPEILSSTAMNDPSQASLINHQQDGPNFHCGT
EEVHACHDGSDFFNFGKWNEIQPNDIDGDTLMKSGCNRNLSRGSECSLGIFD
DLMFKDWALNHCPEDNATLDLESLAHLLDSEEWP

FIG. 22

SEQ ID NO: 17  Amino acid sequence of MYB domain

LNRGAWTALEDKILTAYIKAHGEGKWRNLPKRAGLKRCGKSCRLRWLN
YLRPDIKRGNISNDEEELIVRLHKLLGNRWSLIAGRLPGRTDNEIKNY
WNTTLGK

FIG. 23

SEQ ID NO: 25 – MYB134 amino acid sequence comprising a single conservative amino acid substitution MGRSPCCSKEGLNRGAWTALEDKILTAYIKAHGEGKWRNLPKRAGLKRCGKSC
RLRWINYLRPDIKRGNISNDEEELIVRLHKLLGNRWSLIAGRLPGRTDNEIKNYWNTTLG
KKATAQASPQSKQNSQSFKKRAIEPMTNTQSSKSTLATQVIPTKATRCTKVFLSLQSPPPP
IPPPKTLSSTAIDDPPQAPLLNHQQDSPNLHCRDDDSDFLNFGHWNEFQPSDGGTLIDND
CDKNLSIDSYHSLAVSDDLMFKDWALNRCLDDNSTLDLESLAHLLESEEWPEMRH

FIG. 24

SEQ ID NO: 26    Amino acid sequence of MYB transcription factor from *P. trichocarpa*

MGRSPCCSKEGLNRGAWTALEDKILTAYIKAHGEGKWRNLPKRAGLKRCGKSCRLRW
LNYLRPDIKRGNISNDEEELIVRLHKLLGNRWSLIAGRLPGRTDNEIKNYWNTTLGKKAT
AQASPQSKQNSQSFKKRAIEPMTNTQSSKSTLATQVIPTKATRCTKVFLSLQSPPPPILPPK
TLSSTAIDDPPQAPLLNHQQDSPNLHGHDDSDFLNFGHWNEFQSSDGGTLIDNDCDKNL
SIDSYHSLALSDDLMFKDWALNRCLDDNSTLDLESLAHLLDSEEWPEMRH

FIG. 25

SEQ ID NO:27    Alternate isolated nucleic acid sequence of *MYB097* atcatcccaatcgaatatattgcttgagcttttgaggaatatagagggagaatagagagaggatgggtagaagtycwam
aggggggmtaattmgaggaacttggactgctactgaagacaaaattcttacagcatatgttagaaattatggtgaaggg
aactgggctagggttmcaarggaaacaggtctgaagagatgtggcaagagttgcaggcttcgttggctgaattatctaaa
accagatgttaaaagaggaaacattrgcccagatgaagaagatctcattattaggcttcacaagctcttaggcaacagatg
ggctttaatagctggaaggmttccaggtcggacggacaatgagatcaagaattactggaattcaaccttgaaaagaaag
gtacaagctaacgatcaaaaacagcctagaagagggaataaagacacwaaaaaacaaaccagaaagacctcaaywg
gattgratawggcggcaccatgcacaaacagtagtcttccttcaccaccagtcttrgmtgaaaatayagagactgatcag
atyctcacagcatcctccattgaagaaggaaccttggaaaaaatatctgatagmaaatcccaactcaaatgatgagctctt
gctattkactaacgataatgatgtgccttgcaacttcttgatggatcttgatatggggcagatgagcttctctgattttctccaa
actgatatcttctcagatagcaataacatgcttgttaatgggcctgcaccttcttatccagatgaagcttcttygttccccgag
gctatgctgcagaattggatatgtgaggatggctttgracttgaactggctatgggtccytgatcaacgatcactgctttcttt
cttgtcaattcaaggcgattaataagcatgtcttctgcttcttcttcttctttatcattatcctttcttgttccaggttatygasattaa
ataaggggagcagagttcgctcatatatatattcccttttgcctgtttccattttttctcagcatttgaacataagaattccaattag
aataagttgratggtccctgtatggaagaaacggcatgcttttaaytggaacacaaatatccaatctaaaaaaaaaaaaaaa
aaa

FIG. 26

POPLAR TRANSCRIPTION FACTORS

CROSS-REFERENCE TO RELATED APPLICATIONS

This application is a divisional application of U.S. application Ser. No. 12/341,715 filed Dec. 22, 2008, now U.S. Pat. No. 7,714,192 which claims priority to Canadian application number 2,612,655 filed Dec. 21, 2007, all herein incorporated by reference.

FIELD OF THE INVENTION

The present invention relates to a poplar transcription factor and its use in transgenic plants. More specifically, it relates to a transcription factor that regulates the proanthocyanidin pathway, and is a regulator of proanthocyanidin biosynthesis.

BACKGROUND OF THE INVENTION

In response to biotic and abiotic stress, plants activate inducible defense mechanisms. Secondary metabolites that may be toxic to attacking herbivores and pathogens, and protect plant tissues from abiotic stresses, are a common component of induced defenses.

Poplar, for example cottonwoods, poplars, and aspens, hereafter referred to collectively as poplar (*Populus* spp.), has become an important perennial plant. The defense-related phenylpropanoid metabolism of these ecologically important trees is complex. The major defense phenylpropanoids produced in poplar leaves are the flavonoid-derived proanthocyanidins (PAs) and the salicin-based phenolic glycosides (PGs).

PGs and PAs are the most abundant foliar phenolic metabolites in poplar, and together can constitute more than 30% leaf dry weight. Salicin-based PGs are constitutively produced in poplar leaves and function as potent anti-insect herbivore compounds. Although not often rapidly induced by herbivory, PG levels can exhibit considerable genotypic variability and are also influenced by environmental factors such as light and nutrient availability.

PAs are constitutively produced in poplar leaves however; in some genotypes concentrations rapidly increase in response to stress treatments for example insect herbivore feeding, mechanical wounding, defoliation, pathogen infection, and exogenous application of jasmonic acid. PA accumulation following wounding and herbivore attack generally occurs both locally at the site of damage, and systemically in distal leaves. Leaf PA levels are also strongly influenced by environmental conditions. Nutrient limitation and high light levels have been linked to greater PA. Increased PA levels have also been reported in *P. tremuloides* grown under elevated ozone.

Rapid stress-induced production of PAs in poplar leaves typically follows the transcriptional activation of the biosynthetic pathway. The strong activation of the PA biosynthetic pathway following insect herbivore damage suggests that these compounds function in herbivore defense. However, despite being rapidly induced by insect herbivores, experimental evidence indicates that unlike PGs, PAs are not strong, broad-spectrum anti-herbivore compounds.

Regulation of PA biosynthesis has been characterized in *Arabidopsis*, where TT2 regulates PA production specifically in the seed testa, in a tissue dependent manner. Regulation of PA production in *Arabidopsis* seed testa involves biosynthetic gene activation by a MYB-bHLH-WDR complex composed of the TT2, TT8, and TTG1 proteins. The R2R3 MYB protein TT2 confers target gene specificity to the complex, leading to the activation of genes from the late flavonoid pathway for PA biosynthesis, for example BAN (ANR), TT12, and AHA10. AHA10 is a vacuolar ATPase, which is required for PA accumulation in *Arabidopsis* seed coats to energize transport via the tt-12 MATE transporter.

It was shown that TT2 does not regulate the early flavonoid biosynthetic genes, and therefore does not regulate PA biosynthesis independently. TT2 must work in collaboration with other genes. Further, TT2 activity is not correlated with an accumulation of PA and overexpression of TT2 alone does not lead to the accumulation of PAs.

A second PA-specific MYB gene, VvMYBPA1, isolated from grapevine (*Vitis vinifera*) was found to regulate both PA-specific structural genes of the late flavonoid pathway, and early flavonoid structural genes, for example those encoding chalcone synthase (CHS) and chalcone isomerase (CHI). Despite the established role of R2R3 MYB proteins in the developmental regulation of PA biosynthesis, a protein that regulates expression of all of the biosynthetic structural genes and regulates accumulation of PA, has yet to be disclosed.

It is an object of the present invention to overcome the deficiencies in the prior art.

SUMMARY OF THE INVENTION

Exemplary embodiments of the present invention relate to an isolated nucleic acid molecule comprising a nucleotide sequence selected from the group consisting of nucleotide sequences set forth in SEQ ID NO:1, SEQ ID NO:2, SEQ ID NO:3, SEQ ID NO:4, SEQ ID NO:5, SEQ ID NO:6, SEQ ID NO:11, where the nucleotide sequence encodes at least a corresponding amino acid sequence set forth in SEQ ID NO:12, SEQ ID SEQ ID NO:13, SEQ ID NO:14, SEQ ID NO:15, SEQ ID NO:16, SEQ ID NO:17, SEQ ID NO:26. The nucleic acid sequences and corresponding amino acid sequences regulate the flavonoid pathway, and more particularly they further regulate the PA biosynthetic pathway, and further still they regulate proanthocyanidin biosynthesis in a plant. In another embodiment, the nucleic acid sequences and corresponding amino acid sequences further regulate expression of early flavonoid structural genes and PA-specific structural genes of the late flavonoid pathway. The core phenylpropanoid pathway is regulated by the nucleic acid sequences and corresponding amino acid sequences as are the early and late flavonoid pathways. In another embodiment, the nucleic acid sequences regulate the flavonoid pathway in a plant in a tissue-independent manner Another exemplary embodiment relates to an isolated nucleic acid molecule comprising a nucleotide sequence having at least 75%, 80%, 85%, 90%, 95%, 96%, 97%, 98% homology to the nucleotide sequences set forth in SEQ ID NO:1, SEQ ID NO:2, SEQ ID NO:3, SEQ ID NO:4, SEQ ID NO:5, SEQ ID NO:6, SEQ ID NO:11.

A further exemplary embodiment relates to an isolated nucleic acid molecule comprising a nucleotide sequence that is at least one of a full length complement, a fragment, and a synthetic oligonucleotide of the nucleotide sequence selected from the group consisting of nucleotide sequences set forth in SEQ ID NO:1, SEQ ID NO:2, SEQ ID NO:3, SEQ ID NO:4, SEQ ID NO:5, SEQ ID NO:6, SEQ ID NO:11.

One exemplary embodiment relates to an isolated nucleic acid molecule comprising the nucleotide sequence of MYB134 set forth in SEQ ID NO:3.

Another exemplary embodiment relates to an isolated nucleic acid molecule comprising a nucleotide sequence and corresponding amino acid sequence that encode a MYB protein.

A further exemplary embodiment relates to an isolated nucleic acid molecule comprising a nucleotide sequence where expression of the nucleotide sequence modulates an increase in proanthocyanidin in the plant.

Another exemplary embodiment relates to an isolated nucleic acid molecule comprising a nucleotide sequence where the nucleotide sequence is operatively linked to a promoter.

Another embodiment of the present invention relates to methods of producing a transformed plant, where the method comprises introducing into a cell of a plant a nucleic acid sequence selected from the group consisting of SEQ ID NO:1, SEQ ID NO:2, SEQ ID NO:3, SEQ ID NO:4, SEQ ID NO:5, SEQ ID NO:6, SEQ ID NO:11, and regenerating a transformed plant from the transformed cell.

In one embodiment, the host plant cell comprises at least one of the nucleic acid sequences set forth SEQ ID NO:1, SEQ ID NO:2, SEQ ID NO:3, SEQ ID NO:4, SEQ ID NO:5, SEQ ID NO:6, SEQ ID NO:11. In another embodiment the host cell has an increased proanthocyanidin concentration on comparison to an untransformed plant cell of the same species.

A further exemplary embodiment relates to a host plant cell comprising the nucleic acid sequence of MYB134 set forth in SEQ ID NO:3.

In a further exemplary embodiment, the host plant cell is introduced into a forage plant. The forage plant may be selected from the group consisting of sweet clover, red clover, Alsike clover, corn, wheat, barley, oats, alfalfa, and sorghum. In another embodiment, a raw silage contains at least one of the forage plants containing a transformed host cell.

Another exemplary embodiment relates to a protein for regulating the flavonoid pathway, where the protein contains an amino acid sequence selected from the group consisting of amino acid sequences set forth in SEQ ID NO:12, SEQ ID SEQ ID NO:13, SEQ ID NO:14, SEQ ID NO:15, SEQ ID NO:16, SEQ ID NO:17, SEQ ID NO:26.

One exemplary embodiment of the present invention relates to a transformed plant comprising at least one of the nucleic acid sequences selected from the group consisting of SEQ ID NO:1, SEQ ID NO:2, SEQ ID NO:3, SEQ ID NO:4, SEQ ID NO:5, SEQ ID NO:6, SEQ ID NO:11. Further, the transformed plant comprising the nucleic acid of MYB134 set forth in SEQ ID NO:3. In another exemplary embodiment, the transformed plant has an increased proanthocyanidin concentration on comparison to an untransformed plant of the same species. The transformed plant in one embodiment is a forage plant. The forage plant may be selected from the group consisting of sweet clover, red clover, Alsike clover, corn, wheat, barley, oats, alfalfa, and sorghum.

BRIEF DESCRIPTION OF THE DRAWINGS

Embodiments of the present invention will now be described, by way of example only, with reference to the attached Figures, wherein:

FIG. 11 is the nucleic acid sequence for MYB183;
FIG. 12 is the nucleic acid sequence for MYB086;
FIG. 13 is the nucleic acid sequence for MYB134;
FIG. 14 is the nucleic acid sequence for MYB097;
FIG. 15 is the nucleic acid sequence for MYB087;
FIG. 16 is the nucleic acid sequence for the MYB domain;
FIG. 17 is the nucleic acid sequence for a MYB transcription factor;
FIG. 18 is the amino acid sequence for MYB183;
FIG. 19 is the amino acid sequence for MYB086;
FIG. 20 is the amino acid sequence for MYB134;
FIG. 21 is the amino acid sequence for MYB097;
FIG. 22 is the amino acid sequence for MYB087;
FIG. 23 is the amino acid sequence for MYB domain;
FIG. 24 is the amino acid sequence for MYB134 having a conservative variant;
FIG. 25 is the amino acid sequence for a MYB transcription factor; and
FIG. 26 is an alternative nucleic acid sequence for MYB097.

DETAILED DESCRIPTION OF THE INVENTION

Definitions

Figure 1:
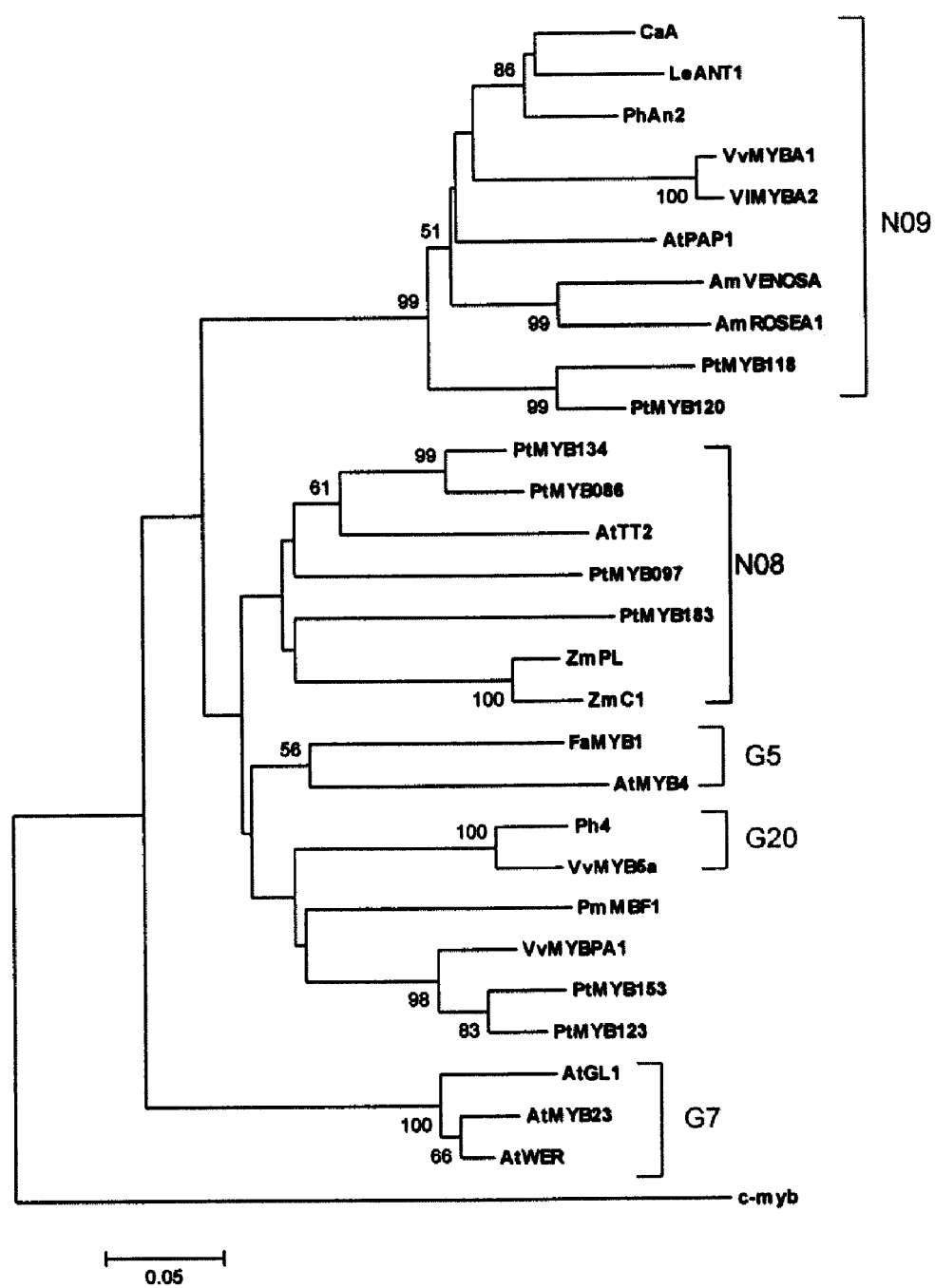
FIG. 1 is a flow chart illustrating the Phylogenetic tree using predicted amino acid sequences of the R2R3 MYB domains.

Unless otherwise noted, technical terms are used according to conventional usage. The following definitions and abbreviations are to be used for the interpretation of the claims and the specifications.

Conservative variants: "Conservative" variants are amino acid substitutions to an amino acid sequence are that do not substantially affect the synthesis of PA. In one example, a polypeptide may include about 1, about 2, about 5, about 10, or about 15 conservative substitutions and retain biological activity. Conservative variation may also include the use of a substituted amino acid in place of an unsubstituted parent amino acid, provided that the required biological activity for PA biosynthesis is retained. Examples of these conservative amino acid substitutions may include:

TABLE 1

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Degenerate variant: A polynucleotide encoding a polypeptide that includes a sequence that is degenerate as a result of the genetic code. There are 20 natural amino acids, most of which are specified by more than one codon. Therefore, all degenerate nucleotide sequences are included as long as the amino acid sequence of the polypeptide encoded by the nucleotide sequence is unchanged.

Specific tissue expression of genes or specific gene expression: Expression of a gene or genes in one tissue or groups of tissues. For example, but not limited to, flower specific, seed specific, leaf specific or root specific, epidermis specific, or parenchyma specific.

Subject: Living multi-cellular vertebrate organisms, a category that includes both human, aquaculture and veterinary subjects, including mammals and fish.

Tissue dependent manner: Refers to expression, activity or accumulation of a gene, protein or product in a specific tissue, or specific tissues. This is also called tissue specific manner. For example, but not limited to, seed specific expression, activity or accumulation.

Tissue independent manner: Refers to the expression, activity or accumulation of a gene, protein or product in a plant that is not specific to a particular tissues or group of tissues. This is also called tissue non-specific manner.

The present invention relates to the MYB domain, and more specifically R2R3 MYB domain transcription factors. The MYB domain, more particularly MYB domain transcription factors, and even more particularly MYB134 regulate both the early and late components of the flavonoid pathway leading to the biosynthesis of PA, as well as general phenylpropanoid enzymes, for example phenylalanine ammonia lyase, cinnamate 4-hydroxylase, and 4-coumarate CoA ligase. More specifically, MYB domain transcription factors regulate the general phenylpropanoid pathway, the flavonoid pathway and the PA biosynthetic pathway. MYB domain transcription factors further regulate the expression of early flavonoid structural genes and PA-specific structural genes of the late flavonoid pathway, more specifically the general phenylpropanoid genes PAL1 and 4CL2, the early flavonoid genes CHS, CHI, and F3H, the late flavonoid genes DFR1 and ANS1, and the PA-specific genes ANR1 and LAR1.

The phenylpropanoid pathway typically begins when the phenylpropanoid enzyme, phenylalanine ammonia lyase (PAL), deaminates phenylalanine to produce cinnamic acid. This compound, cinnamic acid, is further modified by the enzymes cinnamate 4-hydroxylase and 4-coumarate CoA ligase in multiples steps. Thereafter, the compound may enter numerous different pathway branches which flow into numerous other pathways. However, in PA synthesis, the modification of cinnamic acid leads to the synthesis flavan-3-ols in the flavonoid pathway.

The flavonoid pathway is the key pathway involved in PA biosynthesis. The flavonoid pathway and has both early and late pathway components, each of which are involved in genetic regulation and expression of gene products. The early flavonoid genes may include components that encode the enzymes that convert p-coumaroyl-CoA and malonyl-CoA into chalcone and basic flavonoids, for example chalcone synthase, chalcone isomerase, flavanone 3-hydroxylase, and flavonoid 3'-hydroxylase. The late flavonoid pathway components further include the proanthocyanidin pathway (PA pathway). The late flavonoid genes may include dihydroflavonol reductase, leucoanthocyanidin reductase, anthocyanidin synthase, anthocyanidin reductase, and a tt-12-like MATE transporter. Typically, the genes which regulate the PA pathway are the PA-specific structural genes of the late flavonoid pathway.

Several isolated nucleic acid fragments that encode the amino acid sequences of MYB transcription factors, that regulate both the early and late components of the flavonoid pathway have been previously deposited to GenBank (Accession Numbers: FJ573151; FJ573150; FJ573152, 1167121 and Protein ID: 578002 from Gene Model Name: eugene3.00180226, Protein ID: 819461 from Gene Model Name: estExt_fgenesh4_pg.C_LG_VI1485). These nucleic acid sequences are characterized by the nucleotide sequences set forth in SEQ ID NO: 1, 2, 3, 4, 5, 6, and 11. These transcriptions factors are characterized by the corresponding amino acid sequences set forth in SEQ ID NO: 12, 13, 14, 15, 16, 17 and 26. These sequences are found in FIGS. 9 through 22 as detailed in Table 2.

TABLE 2

| SEQ. ID No. | Sequence Name/Type | FIG. No. |
|---|---|---|
| 1 | MYB183/nucleic acid | 11 |
| 2 | MYB086/nucleic acid | 12 |
| 3 | MYB134/nucleic acid | 13 |
| 4 | MYB097/nucleic acid | 14 |
| 5 | MYB087/nucleic acid | 15 |
| 6 | MYB Domain/nucleic acid | 16 |
| 11 | MYB transcription factor/nucleic acid | 17 |
| 12 | MYB183/amino acid | 18 |
| 13 | MYB086/amino acid | 19 |
| 14 | MYB134/amino acid | 20 |
| 15 | MYB097/amino acid | 21 |
| 16 | MYB087/amino acid | 22 |
| 17 | MYB Domain/amino acid | 23 |
| 25 | MYB transcription factor/amino acid | 24 |
| 26 | Alternate MYB183/nucleic acid | 25 |

In another embodiment, the present invention relates to fragments of the MYB domain, more particularly MYB domain transcription factors shown in Table 3, that regulate both the early and late components of the flavonoid pathway leading to the biosynthesis of PA. A fragment of MYB134, MYB086, MYB087, and the MYB domain is set forth in SEQ ID NO. 18. SEQ ID NO. 19 contains a single conservative amino acid substitution at position 1, Arginine (ARG) to Lysine (LYS). SEQ ID NO. 20 contains an additional amino acid base at position 11, Isoleucine (ILE). In a further embodiment, a fragment of MYB097, MYB134, MYB086, MYB087, and the MYB domain is set forth in SEQ ID NO. 21. SEQ ID NO. 22 contains a single conservative amino acid substitution at position 7, Leucine (LEU) to Isoleucine (ILE). SEQ ID NO. 23 contains a single conservative amino acid substitution at position 7, Leucine (LEU) to Valine (VAL). In another embodiment, a fragment of the MYB134 transcription factor has an amino acid sequence set forth in SEQ ID NO: 24.

TABLE 3

| SEQ ID NO | SEQUENCE |
|---|---|
| 18 | RGAWTALEDK |
| 19 | KGAWTALEDK |
| 20 | RGAWTALEDKI |
| 21 | CGKSCRLRWL |
| 22 | CGKSCRIRWL |
| 23 | CGKSCRVRWL |
| 24 | VIPTKATRCT |

Amino acids are the building blocks of proteins, and are linked together in a polypeptide chain by peptide bonds to form a protein chain. Based on the chemical structure of individual amino acids, the protein chain has directionality. The end of the protein with a free carboxyl group is known as the carboxy terminus (C-terminus), and the end with a free amino group is known as the amino terminus (N-terminus).

One exemplary embodiment of the present invention relates to MYB transcription factors and fragments which include at least one of a portion of an N-terminus and a C-terminus. In yet another embodiment, the MYB transcription factors and fragments may further include an additional amino acid residue at the N-terminus portion of the sequence, for example

X--------    (SEQ ID NO: 12-17)

wherein X may be any amino acid. Alternatively, MYB transcription factors and fragments may further include an additional amino acid residue at the C-terminus portion of the sequence, for

--------X    (SEQ ID NO: 12-17)

wherein X may be any amino acid.

One of skill in the art, would understand that given the sequences set forth in SEQ ID NO: 12-17 and 18-24 that conservative amino acid substitutions, as disclosed in Table 1, may produce homologs and variants of MYB transcription factors and fragments that have an amino acid sequence including conservative amino acid substitutions, where the sequence retains the required biological activity for PA biosynthesis. Homologs and variants of MYB transcription factors and fragments, more specifically of MYB134, MYB097, MYB086, MYB087, and the MYB domain, even more specifically MYB134, MYB097 and MYB183 transcription factors may be characterized by possession of at least about 75%, 80%, 85%, 90%, 95%, 96%, 97%, 98% or 99% sequence identity to the parent sequence. One of skill in the art would appreciate that the sequence identity ranges are provided for guidance only. Significant homologs and variants could be obtained that fall outside of the ranges provided, where biological activity is retained.

A further exemplary embodiment relates to a variation in the MYB134 SEQ ID NO: 14. An isolated polypeptide sequence having an amino acid sequence comprising a single conservative amino acid substitution at position 58, Leucine (LEU) to Isoleucine (ILE), is set forth in SEQ ID NO: 25 and illustrated in FIG. 24.

A further exemplary embodiment relates to a MYB transcription factor isolated from *P. trichocarpa*. The isolated nucleotide sequence is set forth in SEQ ID NO: 11 shown in FIG. 17 and the corresponding amino acid sequence set forth in SEQ ID NO: 26 shown in FIG. 25.

The MYB domain transcription factors of the present invention may also include heterologous sequences to the MYB134, MYB097 and MYB183 transcription factors. In one exemplary embodiment, the heterologous sequence is a fusion polypeptide, including at least one of six sequential histidine residues, a β-galactosidase amino acid sequence, and an immunoglobulin amino acid sequence.

One exemplary embodiment of the present invention relates to nucleic acid sequences for modulating, more specifically, increasing PA production in plants. Even more specifically, the present invention relates to increasing PA production in various tree species, particularly trees from the *Populus tremuloides* and *Populus trichocarpa* genome.

$CO_2$ sequestration is the capture and storage of carbon dioxide (usually captured from the atmosphere) in a solid material through biological or physical processes. In plants, photosynthesis provides a type of $CO_2$ sequestration. Photosynthesis is a metabolic pathway that converts light energy into chemical energy where the initial substrates are carbon dioxide and water and the end-products are oxygen and carbohydrates, for example sucrose, glucose or starch. Photosynthesis is one of the most efficient $CO_2$ sequestration processes, plants and particularly trees sequester carbon in their cellulose removing several million metric tons of $CO_2$ equivalents from the atmosphere every year.

Leaves of poplar tress accumulate several classes of phenolic metabolites, including the salicylate-derived phenolic glycosides (PGs), flavonoids such as anthocyanins, proanthocyanidins (PAs, condensed tannins), and flavonol glycosides, and numerous phenolic acids however, PGs and PAs are the most abundant foliar phenolic metabolites. The MYB domain, more particularly MYB domain transcription factors shown that regulate both the early and late components of the flavonoid pathway lead to the biosynthesis of PA. The flavonoid pathway regulates PA synthesis. Increased and overexpression of MYB transcription factors and fragments that correspond to an increase in PA expression further correspond to an increase in PA synthesis in both the above and below ground plant components. PAs from plant roots and leaves accumulate in the trees and in addition, may be incorporated into soil. PAs are generally stable and resistant to microbial degradation such that much of the captured carbon ending up in the PAs is stored and sequestered rather than released back to the atmosphere. Trees having a high PA content exhibit greater rates of carbon sequestration and capture. Trees transformed with the MYB transcription factors and fragments, more specifically MYB134, have a very high capacity for PA synthesis and accumulation.

Another exemplary embodiment of the present invention relates to nucleic acid sequences for modulating, more specifically, increasing PA production in forage crops, for example sweet clover (genus *Trifolium*), red clover (*Trifolium pretense*), Alsike clover (*T. hybridum*), corn, wheat, barley, oats, raw silage, alfalfa, sorghums, and grass legume mix, more specifically alfalfa. Forage refers to the plant material eaten by grazing livestock. It includes both the plants eaten by animals directly as pasture, crop residue, or immature cereal crops and similar plant types harvested and cut for fodder and subsequently carried to animals as hay or silage. An increase in the concentration of PA, within a specific range, in animal feed minimized microbially-generated foaming in livestock which often leads to bloat, and prevents the intake of large volumes of PAs by livestock, which leads to reduced nutrient uptake particularly by ruminants.

The increased expression, or overexpression, of MYB134 in poplar has resulted in the transcriptional activation of the phenylpropanoid pathway, involving 3 enzymes phenylalanine ammonia lyase, cinnamate 4-hydroxylase, and 4-coumarate-CoA ligase, and the flavonoid pathway, leading to a significant plant-wide increase in PA concentration. The increased expression, or overexpression, of MYB134 in plants exhibited a concomitant reduction in the concentration of PG as well as minor alterations to levels of small phenylpropanoids for example, chlorogenic acid. The change in PA concentration in poplar was found to impact both the feeding choice and mortality of early instar forest tent caterpillars (FTC) *Malacosoma distria*, a known widespread herbivore of *P. tremuloides*. The FTC's illustrated a dramatic preference for leaf tissue from MYB134 overexpressing plants. Further, FTC larvae fed a diet of leaf tissue having a higher concentration PA and a lower concentration of PG showed a significantly lower mortality than larvae fed control leaf tissue. Control leaf tissue provides a baseline level for MYB134 expression. FTC are generally specialized herbivores found on native aspen trees that are known to have high tannin levels compared to many other poplars. Typically forest pests such as the gypsy moth for example, generally prefer the low tannin containing trees. Trees transformed with the MYB domain transcription factors and fragments, more specifically MYB134 exhibit higher tannin levels, and in turn, less fewer pest infestations. The higher tannin levels may enable the growth of healthier trees, and in turn, the ability of those trees to sequester greater amounts of $CO_2$.

The present invention further relates to the transformation of host cells, tissues, and plants with at least one of the nucleic acid sequences set forth in SEQ ID NO. 1-6 and 11 that encode proteins that regulates the PA expression. The invention further relates to the use of transformed plant cells and tissues to produce transgenic plants. Methods of producing transgenic plants are well known to those of ordinary skill in the art. Transgenic plants may be produced by a variety of different transformation methods well known in the art for example, electroporation, microinjection, microprojectile bombardment, also known as particle acceleration or biolistic bombardment, viral-mediated transformation, and *Agrobacterium*-mediated transformation. Host cells may be either prokaryotic or eukaryotic.

Where the host is prokaryotic, for example *E. coli*, competent cells capable of DNA uptake are prepared from cells harvested following the exponential growth phase, and subsequently treated using the $CaCl_2$ method using procedures well known in the art. Transformation may also be performed after formation of a protoplast of the host cell, or by electroporation.

Where the host is a eukaryote, methods of transfection of DNA may include calcium phosphate co-precipitates, conventional mechanical procedures for example microinjection, electroporation, insertion of a plasmid encased in liposomes, and virus vectors. Eukaryotic cells may also be co-transformed using the nucleic acid sequences encoding MYB transcription factors and fragments, more specifically MYB134, MYB097, and MYB183 transcription factors and a second foreign DNA molecule encoding a selectable marker for example kanamycin, phosphinothricin, gentamicin, spectinomycin, bleomycin, methotrexate, or sulfonamides. Preferred eukaryotic host cells include any plant species.

In one exemplary embodiment, nucleic acid sequences encoding MYB transcription factors and fragments are transformed with *Malus domestica* (apple) plant cells or plant tissues for example, Golden Delicious or Gala. In further embodiments, the nucleic acid sequences encoding MYB transcription factors and fragments may be transformed with *Medicago sativum* (alfalfa) plant cells or plant tissues, *Lycopersicon esculentum* (tomato) plant cells or plant tissues, *Pyrus communis* L (pear) plant cells or plant tissues, *Trifolium* spp (clovers) plant cells or plant tissues, *Betula* spp (birch) plant cells or plant tissues and *Populus* spp (poplar and aspen) plant cells or plant tissues. In a further embodiment, increased levels of MYB134 expression in transformed plant cells and tissues may be correlated to increased PA expression in those same transformed plant cells and tissues, more specifically transformed Apple cells and tissues. Fruit of apple trees generated from the transformed cells and tissues may be used to provide a healthier fruit snack. Consumption of food exhibiting a high PA content, has beneficially properties linked to the anti-oxidant function of PAs.

The importance of flavonoids in functional foods as mediators of long-term health, is now broadly accepted. Numerous epidemiological studies have documented that diets high in flavonoids reduce the risk of coronary heart disease, and correlate with a reduced incidence of various cancers. PAs are suggested as the most active health-promoting flavonoids. A wealth of biochemical and physiological evidence further supports the health-promoting effects of PAs. These include improved protection of the urinary tract and kidneys. Flavonoids are known to have broad effects largely based on their anti-oxidant capacity. Free radical-scavenging assays indicate that flavonoids have anti-oxidant activity exceeding that of vitamin C and vitamin E several fold. The oxidation of low-density-lipoprotein by oxygen radicals is a key step leading to atherosclerosis and hardening of arteries, and this process is inhibited by flavonoids (Vinson et al. 2002). Overall, it is known in the art that PAs are key components of functional foods, making them excellent targets for metabolic engineering. Dietary PAs are found in tea, grape, chocolate, berry crops and apple, all plants known for anti-cardiovascular disease and health-promoting properties. It would be understood by a person skilled in the art that the ability to regulate and increase production of PAs in functional food provides excellent health benefits.

MYB transcription factors and fragments, more specifically MYB134, MYB097 and MYB183 transcription factors, may be chemically synthesized using standard methods known in the art, or may be produced recombinantly. An exemplary process for polypeptide production is described in Lu et al., Federation of European Biochemical Societies Letters. 429:31-35, 1998. The nucleotide sequences encoding MYB transcription factors and fragments may include DNA, cDNA and RNA sequences. In another embodiment, nucleotide sequences encoding MYB transcription factors and fragments, and more specifically MYB134, further include those nucleic acid sequences that hybridize to SEQ ID NOs: 1-6, and 11, under highly stringent conditions.

In one exemplary embodiment, DNA sequences encoding MYB transcription factors and fragments, more specifically MYB134, MYB097 and MYB183 transcription factors, may expressed in vitro by introducing the sequence of interest into a suitable host cell. The cell may be prokaryotic or eukaryotic. The sequence of interest may also be expressed in any progeny of the suitable host cell. It is known in the art that progeny of a suitable host cell may not be identical to the parental cell. In each of the synthetic and in vitro methods disclosed above, the resultant proteins expressed may further require purification from other proteins or cellular components. A substantially purified protein is at least 60%, 70%, 80%, 90%, 95% or 98% pure.

The nucleotide sequences encoding MYB transcription factors and fragments that are characterized by corresponding amino acids further encodes a protein. Proteins may be modified by a variety of chemical techniques known to persons skilled in the art, to produce protein derivatives having near identical activity as the unmodified proteins. These modified proteins may also further include other desirable properties. For example, the carboxylic acid group of a protein, whether located on a carboxyl-terminus or on a side chain, may be provided in the form of a salt of a pharmaceutically-acceptable cation, esterified to form a $C_1$-$C_{16}$ ester, converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of a modified protein, whether located at the amino-terminal or on a side chain, may be in the form of a pharmaceutically-acceptable acid addition salt, for example HCl, HBr, acetic, benzoic, toluene sulfonic, maleic, tartaric and other organic salts, a modified to $C_1$-$C_{16}$ alkyl or dialkyl amino, or an amide. Hydroxyl groups of the protein side chains may be converted to $C_1$-$C_{16}$ alkoxy or a $C_1$-$C_{16}$ ester using techniques well-known in the art. Phenyl and phenolic rings of the protein side chains may be substituted with one or more halogen atoms, for example fluorine, chlorine, bromine, or iodine, or with $C_1$-$C_{16}$ alkyl, $C_1$-$C_{16}$ alkoxy, carboxylic acids and esters, or amides of the carboxylic acids. Methylene groups of the protein side chains may further include homologous $C_2$-$C_4$ alkylenes. Thiols may be protected with any one of a number of well-recognized protecting groups, such as acetamide groups. Persons skilled in the art will further understand known methods for introducing cyclic structures into proteins to select and provide conformational constraints to the structure that result in enhanced stability.

In a further exemplary embodiment, the present invention relates to peptidomimetic and organomimetic of MYB transcription factors and fragments, more specifically of MYB134, MYB097 and MYB183 transcription factors. The three-dimensional arrangement of the chemical constituents of such peptido- and organomimetics mimic the three-dimensional arrangement of the peptide backbone and component amino acid side chains, resulting in such peptido- and organomimetics of a MYB134 transcription factor having an increased ability to modulate PA biosynthesis.

In another exemplary embodiment, nucleic acid sequences encoding MYB transcription factors and fragments, more specifically MYB134, MYB097 and MYB183 transcription factors, and even more preferably a MYB134 transcription factor may further include a recombinant DNA which is incorporated into a vector, which is in turn incorporated into at least one of an autonomously replicating plasmid, virus, genomic DNA of a prokaryote or eukaryote, a separate molecule for example cDNA that is independent of other sequences.

In a further exemplary embodiment, nucleotide sequences encoding MYB transcription factors and fragments, more specifically a polynucleotide sequence encoding a MYB134, MYB097 and MYB183 transcription factors, may be operatively linked to expression control sequences. Generally, an expression control sequence operatively linked to a coding sequence is ligated such that expression of the coding sequence is achieved under conditions compatible with the expression control sequences. An expression control sequence may further include promoters, enhancers, transcription terminators, a start codon in front of a protein-encoding gene, splicing signal for introns, maintenance of the correct reading frame of that gene to permit proper translation of mRNA, and stop codons.

Materials and Methods

Cloning

*Populus tremuloides* Michx (clone A2) is used for cloning MYB cDNAs and was collected from the vicinity of Edmonton, Alberta, Canada (Haruta et al., 2001). *P. tremula* L.×*tremuloides* Michx. (clone INRA 353-38) was provided by Professor Steve Strauss (Oregon State University, Corvallis, Oreg.). *P. tremula* L.×*alba* L., clone INRA 717-1-B4, were obtained from Dr. Brian Ellis (University of British Columbia, Vancouver, BC). *P. trichocarpa* Torn & Gray× *deltoides* Bartr. (clone H11-11) was obtained from G. Radamaker (Washington State University, Pullman, Wash.). A2, INRA 353-38 and INRA 717-1B-4 were micropropagated in vitro on solid Murashige and Skoog medium (MS medium), while H11-11 were macropropagated from greenwood cuttings. Plants were maintained in the University of Victoria's Bev Glover Greenhouse and supplemental fertilizer and light as described in Major and Constabel (New Phytologist, 2006, 172:617-635).

Sequence Alignment

Nucleotides were counted over the full length of sequence alignments with the amino acid sequence using the NCBI Blast 2.0, gapped blast set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the interne. One of skill in the art will appreciate that these sequence identity ranges are provided for guidance only; it is entirely possible that strongly significant homologs could be obtained that fall outside of the ranges provided.

Phylogenetic Analysis and Cloning of Putative Poplar PA-Regulatory R2R3 MYB Genes The nucleotide sequence of EST CN192773 and the amino acid sequences of *Arabidopsis* TT2 and *Z. mays* C1 protein sequences were used to query GenBank for highly similar poplar EST sequences. This search resulted in identification of a number of EST sequences representing four different R2R3 MYB gene transcripts with high sequence similarity to AtTT2 and ZmC1. These sequences were assembled into contigs and primers for amplifying full-length sequences designed using Vector NTI Advance version 9.0 (Invitrogen). This software was used to design all primers used in this study. Primer sequences are listed in Table 4. Full-length coding sequences were amplified from cDNA made from *P. tremuloides* (clone A2). Total RNA was isolated from leaves and cloned into pGEM-T Easy (Promega) for sequencing. For multiple sequence alignments and phylogenetic analysis, sequences were aligned using ClustalW (Chenna et al., Nucleic Acid Research, 2003, 31:3497-3500) and formatted using BoxShade. The phylogenetic tree was constructed using the neighbor-joining (NJ) method known in the art, with the minimum evolution test and p-distance model having 1000 bootstrap replicates using the Molecular Evolutionary Genetics Analysis (MEGA) package version 3.1 (Kumar et al., Briefings in Bioinformatics, 2004, 5:150-163). The N08, N09, G5, and G20 subgroups of Jiang et al. (2004) are indicated. GenBank Accession numbers for each element in the phylogenetic tree are as follows: CaA (*Capsicum annuum* A, AJ608992), LeANT1 (*Lycopersicon esculentum* ANT1, AAQ55181), PhAN2 (*Petunia×hybrida* AN2, AAF66727), VvMYBA1 (*V. vinifera* MYBA1, BAD18977), VvMYBA2 (*V. vinifera* MYBA2, BAD18978), AtPAP1 (*A. thaliana* PAP1/MYB75, AAG42001), AmVENOSA (*Antirrhinum majus* VENOSA, ABB83828), AmROSEA1 (*Antirrhinum majus* ROSEA1, ABB83826), AtTT2 (*A. thaliana* TT2/MYB123, Q9FJA2), ZmC1 (*Zea mays* C1, AAK09327), ZmPL (*Z. mays* PL, AAB67721), FaMYB1 (*Fragaria×ananassa* MYB1, AAK84064), AtMYB4 (*A. thaliana* MYB4, NP_850879), Ph4 (*P.×hybrida* PH4, AAY51377), VvMYB5a (*V. vinifera* MYB5a, AAS68190), PmMBF1 (*Picea mariana* MBF1, AAA82943), VvMYBPA1 (*Vitis vinifera* MYBPA1, AM259485), AtGL1 (*A. thaliana* GLABROUS1, P27900), AtMYB23 (*A. thaliana* MYB23, NP_198849), AtWER (*A. thaliana* WEREWOLF 1, NP_196979) c-myb (*H. sapiens* c-myb, AAB49039). B. Alignment of predicted poplar PA regulatory MYB proteins with the *Arabidopsis* PA-regulator TT2, *Zea mays* PL, and uncharacterized MYB proteins from *Oryza sativa* (OsMYB3, GenBank Acc. no. BAA23339) and *Gossypium hirsutum* (GhMYB36, GenBank Acc. no. AAK19617) containing conserved motifs C-terminal to the MYB DNA-binding domain.

Cloning of PtMYB134 and Plant Transformation

The coding sequence of PtMYB134 was PCR-amplified from a *P. tremuloides* (clone A2) cDNA library with primers (Table 2) containing restriction linker sites for subcloning into the vector pBI-524 between the double cauliflower mosaic virus (CaMV) 35S promoter with alpha mosaic virus RNA4 transcriptional enhancer sequence and the nopaline synthase terminator sequence (Datla et al., Plant Science, 1993, 94:139-149).

TABLE 4

| SEQ ID No. | Name | Sequence |
|---|---|---|
| 7 | MYB134 forward primer | CCATGGGGAGGAGTCCATGTTG |
| 8 | MYB134 reverse primer | TCTAGATCATGGCCACTCTTCAGAAT |
| 9 | MYB086 forward primer | AAAGCTCTCAAAGAAAATC |
| 10 | MYB086 reverse primer | GTCTCCGTCTATATCATTT |

The overexpression cassette was then subcloned into the pRD400 binary plasmid carrying the neomycin phosphotransferase II (nptII) gene for kanamycin resistance (Datla et al., Gene, 1992, 122:383-384). The binary vector pRD400-PtMYB134 was transferred to the *Agrobacterium tumefaciens* strain C58 (pMP90) (Koncz and Schell, Molecular & General Genetics, 1986, 204:383-396). The pRD410 plasmid containing the β-glucuronidase (GUS) gene was used as a control construct (Datla et al., 1992). Hybrid aspen (*P. tremula×tremuloides* clone INRA 353-38 and *P. tremula×alba* clone INRA 717-1B-4) were transformed using the protocol of Leplé et al. (Plant Cell Reports, 1992, 11:137-141). Positive independently transformed lines were identified by selection of shoots from separate explants on kanamycin-containing rooting medium, and confirmed by PCR analysis and Southern blot analysis using a probe complimentary to the neomycin phospho-transferase II gene present on the T-DNA.

Light Stress Treatments & Wounding

Figure 3A:
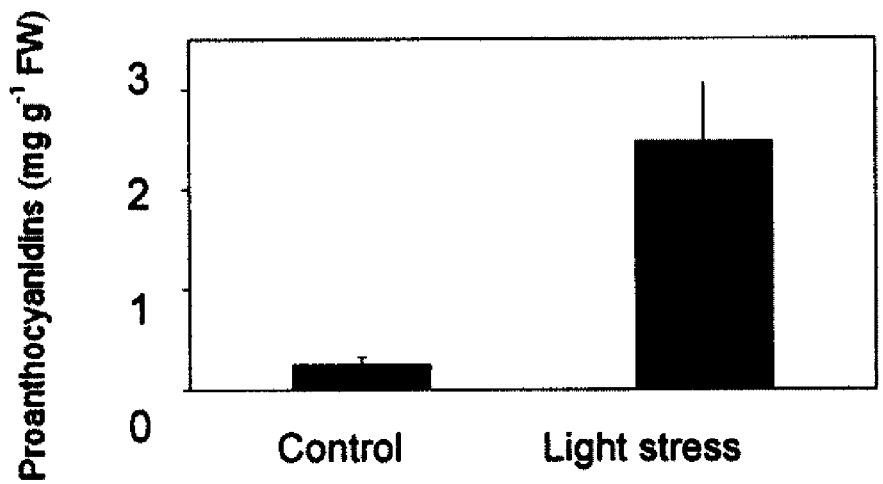
FIG. 3A is a bar graph illustrating the proanthocynanidin content in light stressed leaves analyzed by the acid butanol method.
Figure 3B:
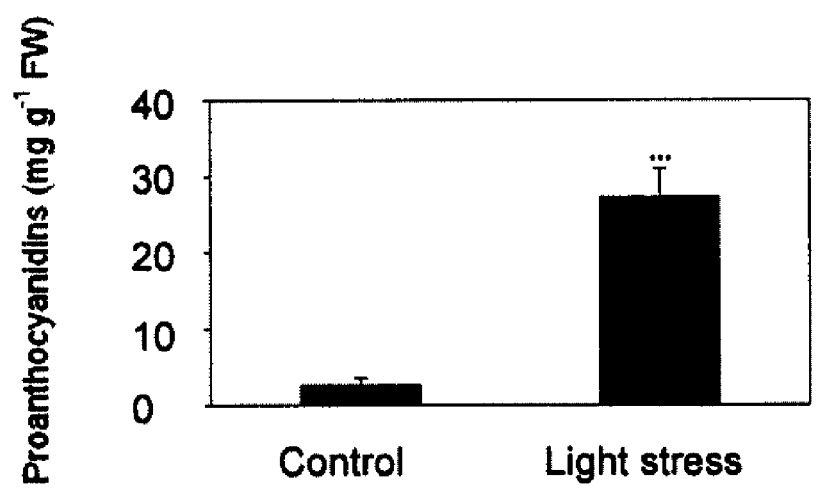
FIG. 3B is a bar graph illustrating the proanthocynanidin content in light stressed leaves analyzed by HPLC.

Twelve week-old plants were used to conduct stress experiments and analysis of transgenics. All stress treatments were applied at 11:00 am, the 0 h time-point in FIGS. 3 and 4. A separate plant was used for each time point, and leaf tissue with mid veins and damaged tissue removed was frozen in liquid nitrogen and stored at −80 C until analyzed. Odd numbered leaves within the specified range were harvested for RNA extraction and even numbered leaves were harvested at later time points for phytochemical analysis.

PAs were quantified using the acid-butanol method and total flavonol glycosides were quantified as rutin equivalents using HPLC-DAD. Phytochemicals are expressed as mg/g fresh weight. The quantified data was plotted as a mean of 4 (flavonol glycoside analysis) or 7 (PA analysis) plants per treatment, with error bars indicating the SE of mean.

Leaf margins were crushed with pliers at leaf plastochron index (LPI) 9-15 (Leaf plastochron index, Larson and Isebrands, 1971). For light stress experiments, plants were moved from the greenhouse, having a mean maximum photosynthetically active radiation (PAR, 400-700 nm) of 377 mol m$^{-2}$ s$^{-1}$ and a biologically effective ultraviolet-B irradiance (UV-B$_{be}$) of 0.26 kJ m$^{-2}$ 6 hr day$^{-1}$, into full natural sunlight, having a mean maximum PAR of 1655 mol m$^{-2}$ s$^{-1}$ and UV-B$_{be}$ of 3.48 kJ$^{-1}$m$^{-2}$ 6 hr day$^{-1}$. The combined wounding/light stress experiment shown was conducted in August 2005, and replicated with equivalent results in October 2006. The semi-quantitative Real-Time PCR (RT-PCR) analysis with gene-specific primers was run on multiple representative samples from both experiments. The independent wounding/light stress experiments analyzed with real time PCR were conducted in August 2005.

UVB Treatment

Trees were acclimated for a period of one week in a growth chamber (16/8 hr photoperiod, 19-25° C.) equipped with F40T12 lamps (Phillips Lighting Company, Somerset, N.J.) with pre-solarized cellulose acetate filters to block UV-C transmission before turning on UV-B lamps for 6 hours per day (0.21 kJ m$^{-2}$ 6 hr day$^{-1}$ UV-B$_{be}$ before UV-B lamps were activated and 1.45 kJ$^{-1}$ m$^{-2}$ 6 hr day$^{-1}$ UV-B$_{be}$ irradiance after the lamps were activated). Measurements of UV-B$_{be}$ were made with an IL1700 radiometer equipped with a IL782A high gain photo-multiplier (International Light, Newburyport, Mass.) using weighting factors from the Caldwell action spectrum normalized to 300 nm (Bjorn and Teramura, Environmental UV Photobiology, 1993, Plennum Press, p 41-71.)

Plant Growth Conditions

Hybrid poplar were inoculated with *Melampsora medusae* Thümen spores as described in Miranda et al. (2007). For phytochemical analysis of control and MYB134 overexpressing *P. tremula×tremuloides* apical leaves (leaves above LPI 0), petioles (of leaves LPI 9-11), bark (peeled off stem in the region of leaves LPI 10-20), wood (with bark removed from the region of leaves LPI 10-20), old root (within 3 cm of base), and young root (within 3 cm of root tips), samples were rinsed with distilled H$_2$O, blotted dry, frozen on dry ice, and stored at −80 C until analyzed. As would be known to one skilled in the art, accumulation of PA in the various tissues is positively correlated with increased expression of the genes encoding the enzymes of the PA biosynthetic pathway.

Phytochemical Assays and HPLC Analysis

For HPLC analysis 0.50 g frozen leaf tissue was ground in liquid nitrogen and extracted for a period of 4 hours in 10 mL of 80% methanol. Extracts were centrifuged to remove solid debris, then methanol was removed using a rotary evaporator, followed by clean-up with Strata-X 33 μm solid phase extraction columns (Phenomenex, Torrence, Calif.) according to the manufacturer's instructions. Compounds were eluted in 2 mL of methanol:acetonitrile (1:1, v/v), and 30 uL injected into an diode array detector-equipped HPLC system (Beckman Coulter System Gold 126 Solvent Module with a System Gold 168 detector, Beckman Coulter, Inc. Fullerton, Calif.) with a reversed phase Luna C18(2) column (250×60 mm, 5μ; Phenomenex, Torrence, Calif.). Reverse phase-HPLC separation was performed with a linear elution gradient from a 90% solvent A (0.5% methanol in 0.01 M phosphoric acid, v/v) to a 40% solvent B (100% acetonitrile) over 30 minutes at a flow rate of 1.5 mL min$^{-1}$. This method does not permit precise identification of compounds however, peaks may be assigned to different subclasses of phenolic compounds based on comparison to the UV absorption spectra of representative standards, as described in Maata et al. (2001). Phenolic acids were quantified as chlorogenic acid (Sigma) equivalents. Flavonol glycosides were quantified as rutin (Sigma) equivalents. Quercetin, myricetin, and kaempferol (Sigma) standards were also used to identify the aglycones in acid-hydrolyzed extracts. Flavan-3-ols were identified by comparison to the absorption spectra and retention time of catechin and epicatechin standards (Sigma), and the putative flavonone/dihydroflavonol was identified using the spectrum of dihydroquercetin (Sigma) and published spectra. Phenolic glycosides were quantified using purified tremulacin, tremuloidin, and salicortin provided by Professor Richard Lindroth (University of Wisconsin-Madison, Madison, Wis.) and Dr. Thomas Clausen (University of Alaska, Fairbanks). Proanthocyanidins were assayed using an acid butanol (BuHCl) assay. In this assay, PAs react to give a colored product, which are read in a spectrophotometer at 550 nm. Purified aspen PA is used as a standard as described by Porter et al. (Phytochemistry, 1986, 25:223-230). Purified *P. tremuloides* proanthocyanidin was used as a standard. Relative levels of total soluble phenolics were determined using the Folin-Ciocalteau method (Singleton and Rossi, 1965). PA concentrations in leaves are expressed in mg/g of fresh weight (FW).

RNA Extraction and Expression Analysis

RNA for northern and PCR analyses was isolated from leaf tissue using the cetyltrimethylammonium bromide (CTAB) method as described in Haruta et al. (Plant Molecular Biology, 2001, 112:552-558). Northern analysis was performed using the Church method known in the art, and $^{32}$P-labeled DNA probes. For phenylpropanoid biosynthetic genes, sequence fragments were amplified and cloned into pGEM-T Easy (Promega) from *P. tremula×tremuloides* (INRA 353-38) cDNA using primers selected based on predicted coding sequences available from the DOE Joint genome project database version 1.1 (genome.jgi-psf.org/Poptr1_1) or in GenBank. Full-length MYB gene coding sequences were isolated using methods known in the art. Primers used for amplification and cloning of northern probe templates and PCR analyses are listed in Table 4. $^{32}$P-labeled probes were synthesized with the Rediprime II labeling kit (Amersham) using Qiaquick (Qiagen, Missisauga, ON) purified DNA template fragments. The DFR1 and PAL2 probes were synthesized from cloned fragments described in Peters and Constabel (Plant Journal, 2002, 32:701-712).

For semi-quantitative RT-PCR and real-time PCR analysis, 25 μg of total RNA was treated with Deoxyribonuclease I (Invitrogen, Carlsbad, Calif.) as described in the manufacturer's instructions. 5 μg DNAse I-treated RNA was then used for RT with SuperScript II reverse transcriptase (Invitrogen) to generate cDNA for semi-quantitative and real-time PCR. For semi-quantitative RT-PCR, reactions and amplification conditions were as described below, with the exception that reactions were run for 20 and 30 cycles and Taq polymerase was used according to the manufacturer's instruction (Invitrogen).

Real-time PCR analysis was performed using a Stratagene Mx4000 (Stratagene, La Jolla, Calif., USA). Triplicate reactions were run on biological triplicates using independent experiments conducted at different times. 15 μL, reactions were set up using the QuantiTect™ SYBRGreen mix (Qiagen, Missisauga, ON) with 0.67 μM gene-specific primers and 6.25 ng of cDNA template per reaction. The amplification protocol was 95° C. for 15 min, followed by 40 cycles of 94° C. for 30 s, 55° C. for 40 s, and 72° C. for 60 s. Dissociation curves were obtained to confirm that single, specific products were produced in each reaction. Cycle threshold (Ct) values were determined by Mx4000 software at a manually set fluorescence threshold of 0.019. ΔCt was determined by normalization using the Actin gene ($\Delta Ct = Ct_{goi} - Ct_{actin}$) and relative transcript abundance determined using the formula $2^{-\Delta Ct}$.

Forest Tent Caterpillar (FTC) Bioassays

FTC, *Malacosoma disstria* Hubner, egg bands were obtained from Barry J. Cooke (Canadian Forest Service, Edmonton, AB) and stored at 2° C. until use. Egg masses were sterilized with a 1% bleach solution. Larvae were placed directly onto an artificial diet prior to transfer into 9 cm diameter Petri dishes for the choice and no choice experiments.

For each "choice" experiment, a MYB134 overexpressing transgenic line was paired with a control line. Three high-PA *P. tremula×tremuloides* (clone INRA 353-38) MYB134 overexpressing (P. t.×t MYB-OE lines 3-5, FIG. 5A) and the four 353-38 GUS control (P. t.×t GUS lines 1-3, FIG. 5A) lines were used in all experiments.

Leaves of plastochron index 10-20 harvested from their respective plants were rinsed in distilled water and leaf disks of 2.1 cm$^2$ were cut from the leaves using a cork borer. Leaf disks from one transgenic line and its corresponding control line were placed in the same Petri dish, five disks of each for a total of ten disks. Leaf disks were arranged at the perimeter of the dish, alternating transgenic and control. Four repetitions of each pair were performed, for a total of twelve dishes per experiment. All choice experiments ran for two days. Each dish contained between four and eight early instar larvae depending on the experiment: four larvae in experiment 1, eight larvae in experiment 2, and seven larvae in experiment 3. Larvae were hatched between six and fifteen days prior to the start of the experiments: fourteen to fifteen days for experiment 1, eight days for experiment 2, and six to seven days for experiment 3. Larvae were placed in the centre of the dish. Dishes were lined with Whatman #1 filter paper wet with 1 mL of distilled water and sealed with Parafilm tape. Leaf disk area eaten was measured using an area meter and results were expressed as a mean percentage leaf area consumed.

For each no-choice bioassay, three high PA accumulating P. tremula×tremuloides MYB134 overexpressor (MYB-OE) and three control (GUS) lines were used (exp. 1 and 2: P. t.×t MYB-OE lines 2-4 and P. t.×t GUS lines 1-3; exp. 3: P. t.×t MYB-OE lines 3-5 and P. t.×t GUS lines 1-3, FIG. 5A). For each line, there were 4 replications. Each consisted of a Petri dish lined with Whatman #1 filter paper, wet with 1 mL of sterilized dH$_2$O, on which four leaf disks of one line were clustered in the centre, about 5 mm apart from one another. Five larvae were placed in the center of the dish amongst the clustered leaf disks. Larvae were hatched 24 hours (experiment 1), five days (experiment 2), or 7 days (experiment 3) prior to the bioassays. Larvae killed in transfer, as observed 24 hours from the beginning of the experiment, were removed and replaced. Leaves harvested were between LPI 10 and 20. Leaves that were in poor condition were skipped. Newly hatched larvae typically exhibited relatively high mortality when reared on mature tough leaf material, than with very young leaf material on which larval mortality is much lower. Leaf disks of 1.5 cm diameter were cut from the leaves of each plant using a cork bored. Experiments were run for 8 days, with leaf disks being replaced every two days. Sterilized dH$_2$O was added to the filter paper of each dish as required and dishes sealed with Parafilm tape. Larvae mortality was monitored every two days. Larvae that had died were removed, but not replaced, except for those that had died immediately after transfer to the dish.

The foregoing are exemplary embodiments relating to the present invention. As would be known to one skilled in the art, variations that do not alter the scope of the invention are contemplated. Many biological functions have been proposed for PAs in plants, including protection against insects and larger herbivores through feeding deterrence and reduced food quality, protection against fungal and bacterial pathogens through antimicrobial properties, protection against photodamage and oxidative stress by functioning as antioxidants, UV-B sunscreens, and chelators of redox active metal ions, and storage of excess carbon. Animal feed, such as alfalfa containing feeds, comprising high levels of PAs have been shown to reduce bloat. Similarly, humans can benefit from sunscreens derived from tissues with high PA content. Transformation of plants, including trees to provide enhanced PA production thereby improving the foregoing biological functions are contemplated.

EXAMPLES

Example 1

Identification of Putative PA Regulatory R2R3 MYB Genes in Poplar

A sequence predicted to encode an R2R3 MYB domain transcription factor was previously isolated from a systemically wounded P. trichocarpa×deltoides (clone H11-11) leaf EST sequencing project (GenBank Accession no.: CN192773). The predicted protein encoded by this transcript exhibits high sequence similarity to the N08 MYB as shown in FIG. 1. This subgroup includes the Arabidopsis PA regulator TT2 as well as Z. mays C1, which has also been shown to activate the Arabidopsis BAN promoter. In order to identify candidate regulators of stress-induced PA metabolism in poplar, the cDNA corresponding to CN192773 as well as additional poplar homologues of TT2 was cloned. The CN192773 EST sequence and the Arabidopsis TT2 and Z. mays C1 protein sequences were used to query GenBank for poplar EST sequences in the public domain. This search resulted in four contigs corresponding to transcripts predicted to encode MYB transcription factors of subgroup N08. cDNAs corresponding to these genes, which were considered to be putative poplar PA regulatory R2R3 MYB genes, were cloned from P. tremuloides. With the publication of the P. trichocarpa genome, the genomic sequences were identified and found to correspond to the gene models MYB097 (corresponding to the EST CN192773), MYB086, MYB134, and MYB183. The genome sequence contains two additional copies of the MYB086 gene with about greater than 98% nucleotide identity within the coding sequences, MYB087 and MYB104 collectively referred to as the MYB086 family. This gene family is very similar to MYB134, sharing about 84% nucleotide coding sequence identity with the exception of several insertions/deletions.

A phylogenetic tree was constructed using the predicted amino acid sequences of the R2R3 MYB domains of putative poplar flavonoid regulatory MYBs as well as a selection of R2R3 MYB proteins from other species as illustrated in FIG. 1. The four putative PA regulatory MYBs, specifically MYB097, MYB086, MYB134, and MYB183 are clustered within the N08 group rather than other flavonoid regulatory MYB subgroups, such as N09, G20 or G5. The N09 subgroup is composed of MYB proteins that function as anthocyanin activators, including Arabidopsis PAP1 and P. hybrida AN2. Members of subgroup G5 include negative regulators of phenylpropanoid and flavonoid metabolism. The G20 group includes members involved in controlling vacuolar pH and flavonoid biosynthetic gene activation. A systematic examination of the P. trichocarpa genome led to the identification of additional MYB genes sharing high sequence similarity to other activators of flavonoid metabolism, including MYB123, MYB153, MYB118 and MYB120. MYB118 and MYB120 cluster with anthocyanin regulators of subgroup N09. The MYB123 and MYB153 genes are close poplar homologues to the V. vinifera PA regulator VvMYBPA1 and thus may be involved in PA regulation in poplar.

The MYB134/Arabidopsis tt-2 percent amino acid sequence identity is about 40.8%, and 75.2% is within the MYB domain. The DNA % identity is about 48.6%.

The MYB183/Arabidopsis tt-2 percent amino acid sequence identity is about 41.8%, and 67.2% is within the MYB domain. The DNA % identity is about 51.2%.

The MYB097/Arabidopsis tt-2 percent amino acid sequence identity is about 56.2% within the MYB domain. The DNA % identity is about 64%.

The MYB183/MYB134 percent amino acid sequence identity is about 39.5%, 75.4% within is the MYB domain. The DNA % identity is about 50.9%.

The MYB097/MYB134 percent amino acid sequence identity is about 40.3%, 66.4% is within the MYB domain. The DNA % identity is about 47.3%

R2R3 MYB proteins are characterized by two imperfectly repeated amino-terminal amino acid MYB domains each forming DNA-binding helix-turn-helix structures. Outside of the MYB domain, R2R3 MYB proteins are highly divergent with the exception of short conserved amino acid sequence motifs that form the basis of their classification into different subgroups. MYB134 and MYB086 encode proteins with a motif similar to the $Vx_2IRTKA[IL]RC[SN]$ motif located C-terminal to the MYB domains in Arabidopsis TT2 and O. sativa MYB3. MYB134 and MYB086 also share an additional C-terminal motif with the consensus DL[ED]SLA[HF]LL[ED]$x_2$EWP with uncharacterized MYBs such as Gossypium hirsutum MYB36 (GenBank Acc. no. AAK19617) (FIG. 1) and Malus×domestica MYB9 (GenBank Acc. no.: DQ267900). The $[DE]Lx_2[RK]x_3Lx_6Lx_3R$ motif is involved in the interaction of MYB proteins with bHLH partners and is present in all four putative PA regulatory MYBs, namely MYB134, MYB097, MYB183 and MYB086, indicating that like AtTT2 these MYBs require the presence of bHLH cofactors to function.

Example 2

Figure 2A:
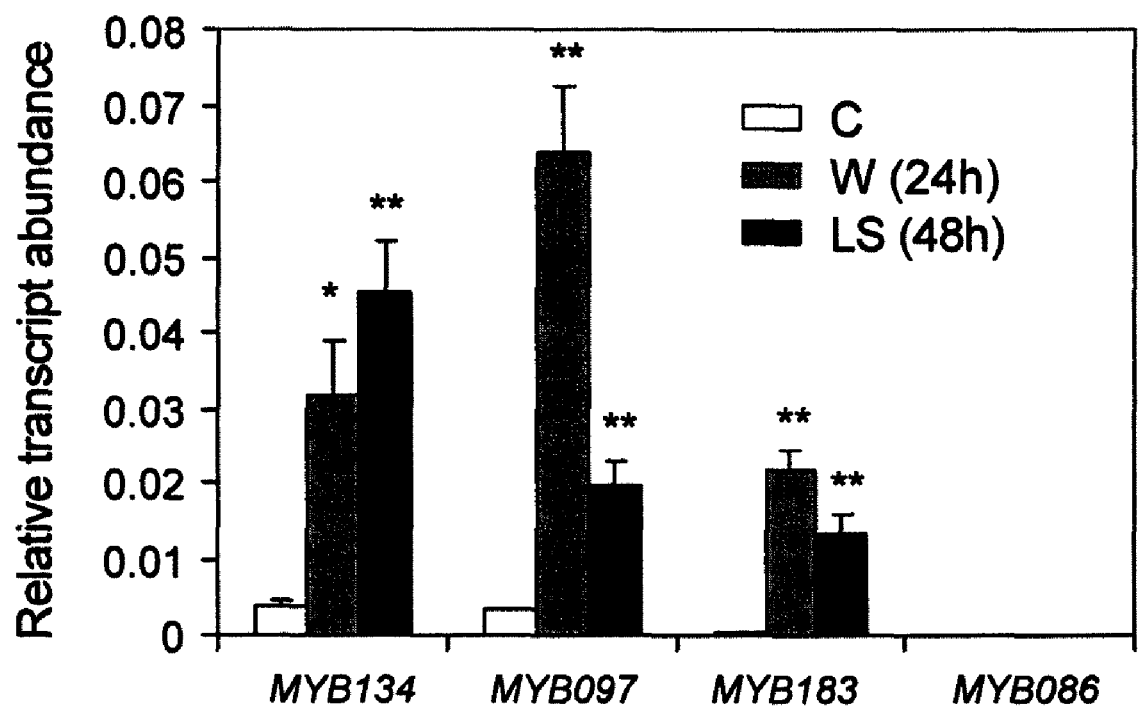
FIG. 2A is a bar graph illustrating the Real-Time Polymerase Chain Reaction (RT-PCR) expression of putative proanthocynanidin regulatory MYB genes.
Figure 2B:
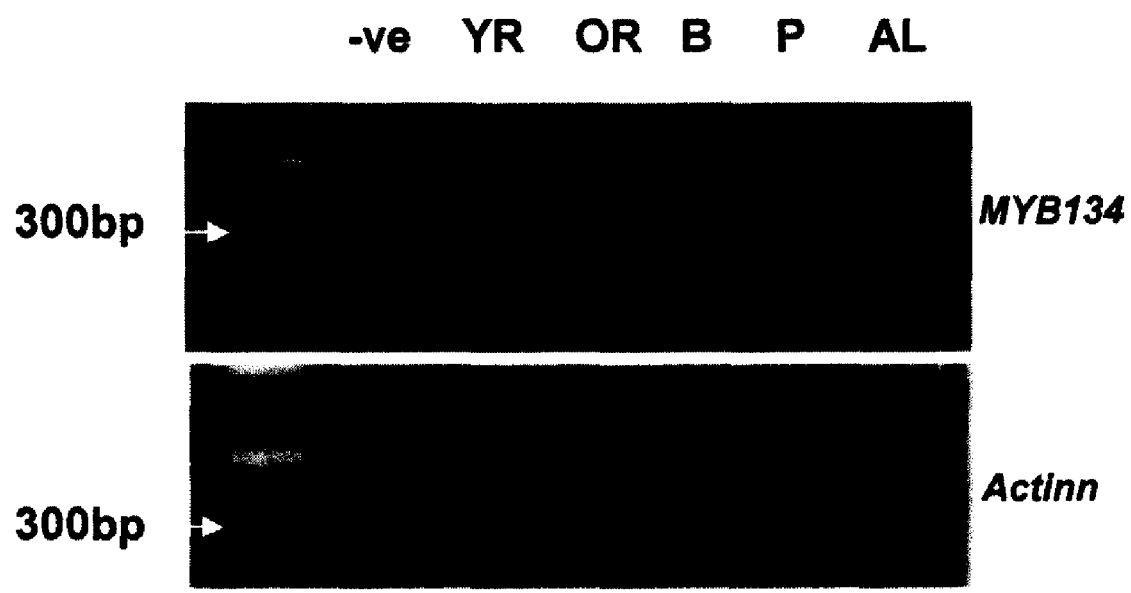
FIG. 2B is a semi-quantitative RT-PCR analysis showing MYB134 expression in selected poplar tissues.

Expression of MYB Genes Under Control Conditions and Under Flavonoid-Activating Stress Semi-quantitative RT-PCR with DNAse-treated RNA illustrated that MYB134 was expressed in young roots (YR), old roots (OR), bark (B), petioles (P), leaves, and shoot apices including apical leaves (AL) as shown in FIG. 2B. This analysis shows MYB134 expression in numerous selected poplar tissues and indicates a plant-wide increase in PA concentration. cDNA was synthesized from DNAse-treated RNA and reaction conditions and gene-specific primers were prepared as for qPCR analysis, with the exception that reactions were run for 28 cycles. This indicates that MYB expression is not tissue specific and in turn that MYB expression, specifically MYB134 expression regulates the flavonoid pathway in a tissue independent manner.

Wound Stress

Figure 9:
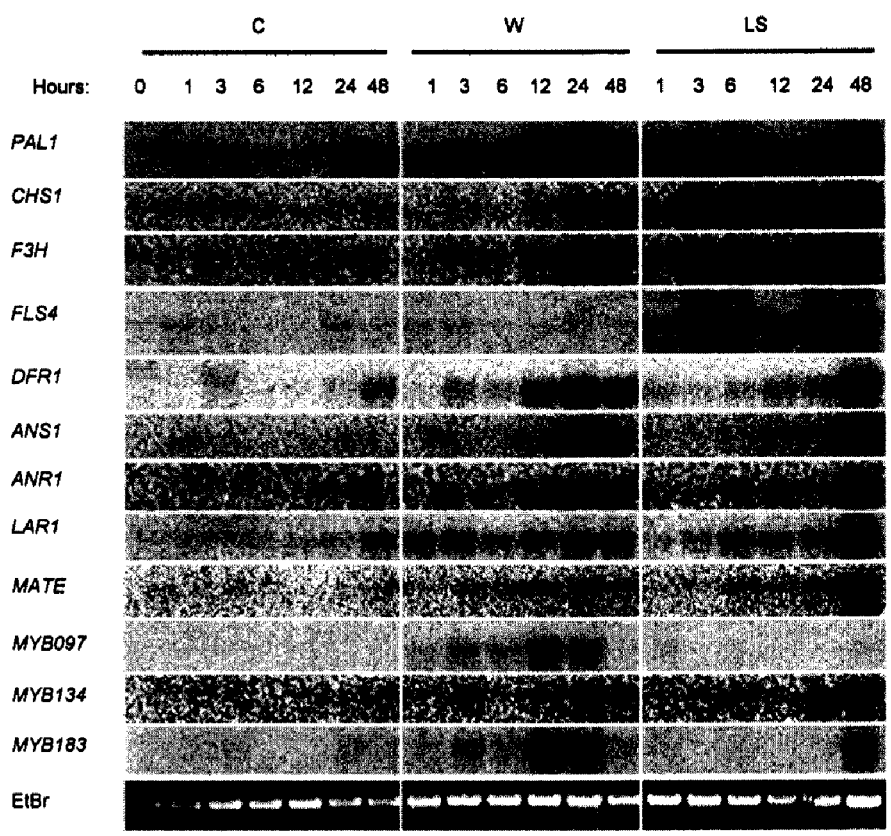
FIG. 9 is a Northern Blot illustrating the expression and wound responsiveness of flavonoid structural genes and putative PA regulatory MYB genes.

Analysis of wound and herbivore-stimulated activation of poplar flavonoid biosynthetic genes leading to PA accumulation was conducted. In order to identify candidate regulators of wound-induced PA biosynthesis, expression of putative PA regulatory MYB genes, specifically MYB134, MYB097, MYB086, and MYB183, in mechanically wounded leaves of P. tremula×tremuloides was profiled. Expression of flavonoid structural genes and putative PA regulatory MYB genes, specifically MYB134, MYB097, and MYB183 was monitored using northern analysis as shown in FIG. 9. The flavonoid structural gene family members analyzed in these experiments were identified as herbivore and pathogen-induced in previous works and are named accordingly.

Mechanical wounding of leaf margins resulted in an upregulation of phenylpropanoid and flavonoid genes as shown in FIG. 9. PAL1, the wound-inducible flavonoid-specific PAL gene was rapidly upregulated and general flavonoid biosynthetic genes, including CHS, F3H, ANS1, and the DFR1 gene followed similar kinetics. FLS4, a flavonol synthase gene, was not responsive to wounding, while the PA-specific genes ANR1 and LAR1 were upregulated. A putative poplar homologue of the Arabidopsis TT12 gene, encoding a multidrug and toxic compound extrusion (MATE) transporter was also upregulated following mechanical wounding. This gene was previously found to be co-induced with PA biosynthetic genes following infection of hybrid poplar leaves with the fungal biotroph Melamspora medusae.

The putative PA regulatory MYB genes MYB097, MYB134, and MYB183 all exhibited wound-induced transcript accumulation that correlated with the activation of flavonoid structural genes as shown in FIG. 9. Expression and wound responsiveness was analyzed using RT-PCR with primers specific to MYB134 or the MYB086 family. Expression of MYB134 was found to be wound-induced.

To analyze MYB gene expression under a general flavonoid-activating stress, plants were moved from a greenhouse into natural sunlight where they were exposed to elevated levels of both visible and ultraviolet-B (UV-B) radiation, termed "light stress". Intense visible light and UV-B radiation are known to stimulate multiple branches of phenylpropanoid and flavonoid metabolism. Analysis of gene expression in light stressed poplar leaves revealed two distinct patterns of flavonoid structural gene activation. UV-B- and M. medusae-induced activation of the flavonoid biosynthetic pathway and putative PA regulatory MYB genes were analyzed. Northern analysis of phenylpropanoid and flavonoid structural genes as well as putative PA regulatory MYB genes in a control and UV-B-treated (UV-B) poplar leaves, as well as a control and M. medusae-infected leaves at six days post-inoculation (M-6 dpi) are illustrated FIG. 4. A rapid and early activation of the flavonol biosynthetic pathway, including general phenylpropanoid and early flavonoid biosynthetic genes PAL2, CHS1 and FLS4, was followed by a later, strong activation of late PA biosynthetic genes ANR1, ANS1, and LAR1 around 48 hours. The activation of flavonol biosynthesis exhibited a dip in expression levels at 12 hours, corresponding to the absence of the stimulus during the night. None of the putative PA regulatory MYB genes were co-activated with the rapidly induced flavonol biosynthetic genes however MYB134 and MYB183 exhibited a strong co-activation with the late flavonoid biosynthetic genes. This pattern of co-activation indicates that the putative PA MYB genes are less important in flavonol synthesis, however they play a significant role in PA biosynthesis.

Figure 10A:
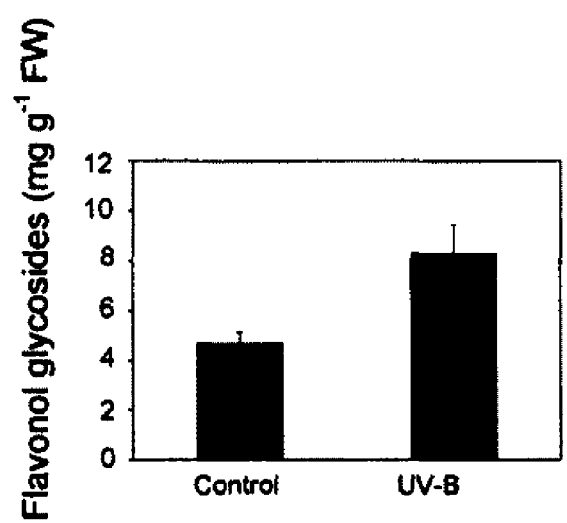
FIG. 10A is a bar graph illustrating PA levels after 7 days of light stress using the acid butanol method; stress.
Figure 10B:
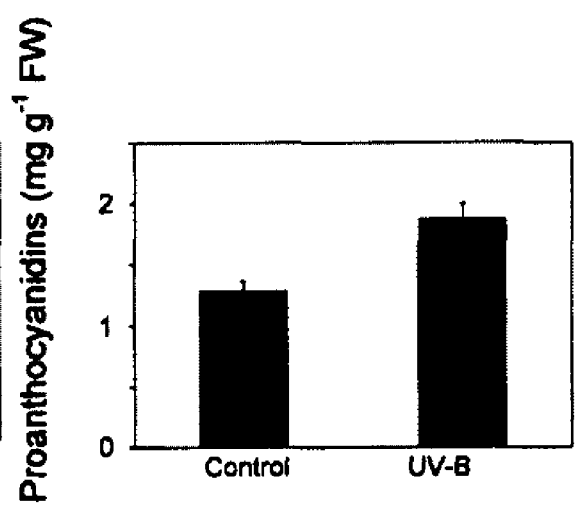
FIG. 10B is a bar graph illustrating an HPLC analysis of PA levels after 7 days of light stress.

Further HPLC analysis of leaves after a period of 7 days of light stress revealed a large increase in the expression of flavonol glycosides (FIG. 10B), corresponding to the strong activation of the flavonol biosynthetic pathway. Analysis of PA expression levels using the acid butanol method also revealed a significant increase after a period of 7 days of light stress (FIG. 10A).

Members of the MYB086 family collectively exhibited a very low, constitutive level of expression, however, each of MYB134, MYB097, and MYB183 exhibited varying levels of expression in both wounded and light-stressed leaves.

To confirm these expression patterns, as well as to ensure that the signals were not the result of non-specific hybridization by the different MYB gene probes, expression of the MYB134, MYB097, and MYB183 was analyzed in leaf tissue 24 hours after wounding and 48 hours after movement into full sunlight using real-time PCR with gene-specific primers. Real-time PCR analysis of putative PA regulatory MYB genes, specifically MYB134, MYB097, MYB086, and MYB183, illustrating relative transcript abundance in a control, 24-hours post wounding, and 48-hours post light stress, is illustrated in FIG. 2A. Asterisks indicate significant differences using Student's t test (* P<0.05,  P<0.01, * P<0.001). This experiment was conducted with triplicate reactions on triplicate independent biological replications. Results indicated that all three MYB genes, MYB134, MYB097, and MYB183 were significantly co-induced with the PA biosynthetic pathway genes under both wounding and light-stress treatments. The very low non-stress-responsive MYB086 family expression was also confirmed. The significant induction of MYB097 in the light stressed leaves analyzed with real-time PCR seemed to contradict the low level of induction in the 48 hour light stressed tree analyzed using northern analysis (FIG. 2A). However, additional replications of this experiment confirmed that activation of the MYB097 gene could be detected with northern analysis, although with a lower fold-induction than MYB134 and MYB183.

Flavonol glycosides are known to be important UV-B protective compounds. Increased flavonol accumulation in leaves has been observed in poplar and other trees under elevated UV-B.

Figure 4:
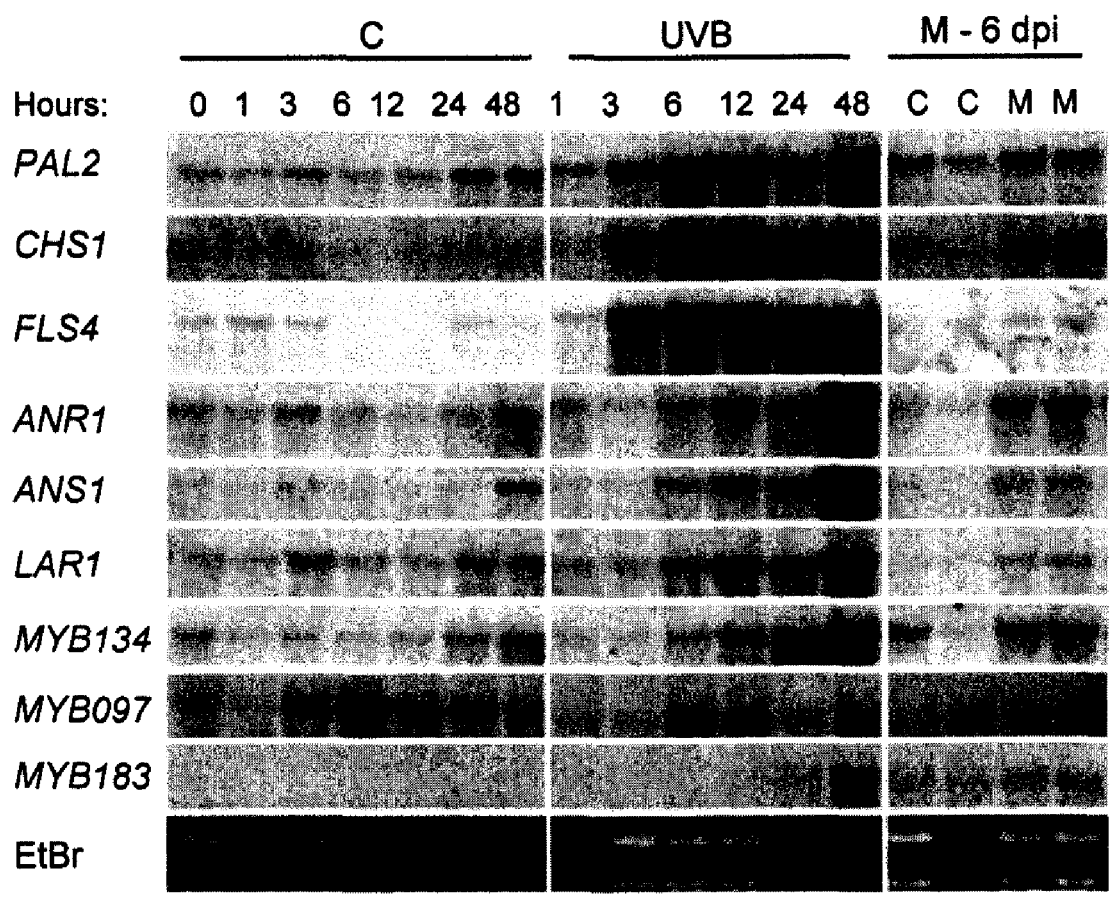
FIG. 4 is a Northern blot illustrating the expression of a plurality of genes.

Flavonoid structural gene activation was examined specifically under elevated UV-B irradiance in controlled conditions in order to assess distinct induction patterns of early and late flavonoid structural genes in the light stressed leaves. The responses of P. tremulaxtremuloides leaves to a sudden increase in UV-B irradiance was monitored following activation of UV-B lamps in a growth chamber, without the visible light stress resulting from movement into full sunlight. Northern analysis of gene expression revealed the same general pattern observed in the light stress experiment disclosed above, including a very rapid activation of flavonol biosynthetic genes, followed by a later strong activation of PA biosynthetic genes (FIG. 4). Concentrations of PA and flavonol glycoside were assessed after a period of 7 days and found to be significantly increased as shown in FIG. 4. None of the poplar MYB genes tested exhibited a rapid co-induction with FLS4 and the early flavonoid biosynthetic genes, while MYB134 was co-induced with the late flavonoid biosynthetic genes. MYB183 showed some upregulation by 48 hours, while MYB097 was not UV-B-responsive (FIG. 4).

Previous analysis of gene expression in M. medusae-infected hybrid poplar (P. trichocarpaxdeltoides, clone H11-11) leaves using a 15.5 K element poplar cDNA microarray illustrated that infection of leaves by this fungal biotroph resulted in a significant upregulation of PA biosynthetic genes at 6 days post-inoculation (dpi), and a corresponding increase in foliar PAs. This PA accumulation contributes to pathogen defense and represents a secondary stress response of the hybrid poplar. Analysis of flavonoid and putative PA regulatory MYB gene expression in leaf tissue 6 days after inoculation with M. medusae spores demonstrated that MYB134 is co-induced with PA structural genes while MYB097 and MYB183 are not strongly induced as illustrated in FIG. 4. FLS4 was not strongly upregulated by M. medusae infection, confirming that expression of MYB134 is not correlated with activation of flavonol metabolism.

Several members of the poplar N08 MYB subgroup, specifically MYB134, MYB097, and MYB183 exhibit stress-induced co-activation with PA biosynthetic genes under some of stress conditions. However, MYB134 expression is the most strongly correlated with PA activation under all stress conditions analyzed. Of the inducible MYB genes, the predicted protein encoded by MYB134 also exhibits the highest homology to TT2 within the R2R3 MYB DNA-binding domain and shares a C-terminal conserved motif. MYB134 is an important regulator of stress-induced PA metabolism Example 3

Figure 5A:
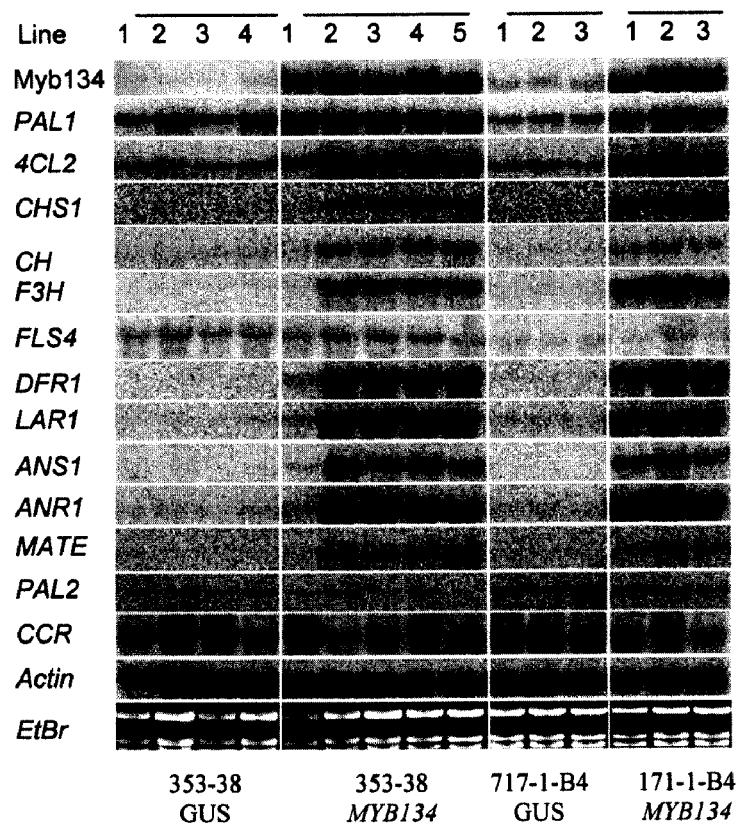
FIG. 5A is a Northern blot illustrating the gene expression.
Figure 5B:
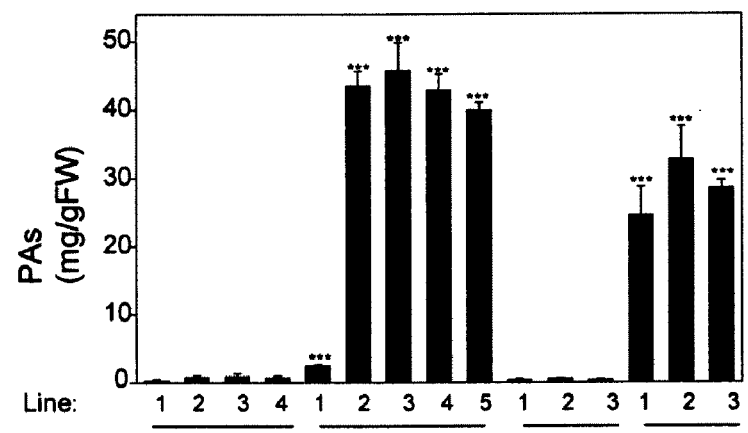
FIG. 5B is a chart illustrating the proanthocynanidin accumulation in transgenic P. tremula×tremuloides and P. tremula×alba.

Effects of MYB134 Overexpression in Poplar on Phenolic Metabolism and Gene Expression In order to investigate the role of MYB134 in the regulation of stress-induced PA metabolism, this gene was overexpressed in poplar under the control of a double cauliflower mosaic virus (CaMV) 35S promoter. β-glucuronidase (GUS) overexpressing lines were produced as controls. Two genotypes, P. tremulaxtremuloides (clone INRA 353-38) and P. tremulaxalba (clone INRA 717-1-B4), were selected to examine MYB134 function because of the differences they exhibit in wound-induced PA metabolism. The P. tremulax tremuloides clone responded to mechanical wounding with transcriptional activation of the PA biosynthetic pathway, while this response has not been observed in this P. tremulax alba clone. Both clones are characterized by very low leaf PA levels under greenhouse conditions. MYB134 overexpressing poplar plants did not exhibit any obvious phenotypic differences when grown under greenhouse conditions. However, analysis of PA expression levels in leaves demonstrated that MYB134 overexpression resulted in a dramatic increase in leaf PA concentration in multiple independently transformed lines of both clones. Northern analysis showed a strong expression of the MYB134 transgene as shown in FIG. 5A, and this expression corresponded to high levels of PA accumulation in leaves as shown in FIG. 5B. FIG. 5 illustrates independently transformed plant lines, the transformation is replicated in each line, which all show the same phenotype. The results show that the observed phenotype is due to insertion of the MYB transgene and is not an artifact of the transformation procedure or one-time event.

In order to confirm that MYB134 activates PA biosynthetic genes, phenylpropanoid structural gene expression was examined in leaves of MYB134 overexpressing plants. MYB134 overexpression was found to activate the phenylpropanoid pathway leading to increased PA production, including the flavonoid specific general phenylpropanoid genes PAL1 and 4CL2 (FIG. 5A). A strong positive correlation between MYB134 gene expression and expression of all the structural genes of the phenylpropanoid pathway was noted. Both early (CHS1, CHI1, and F3H) and late (DFR1, ANR1, ANS1, and LAR1) flavonoid biosynthetic genes were exhibited increased expression however, the level of late PA structural gene activation was much greater (FIG. 5A). The light stress- and UV-B-induced flavonol synthase gene FLS4 was not upregulated. Expression of PAL2 and CCR, genes associated with lignin production, was also not altered in leaves of MYB134 overexpressing plants. Neither MYB183 nor MYB097 were more highly expressed in the MYB134 overexpressing leaves, suggesting that activation of the full suite of PA biosynthetic genes is not mediated by the activation of these genes by MYB134.

Figure 6A:
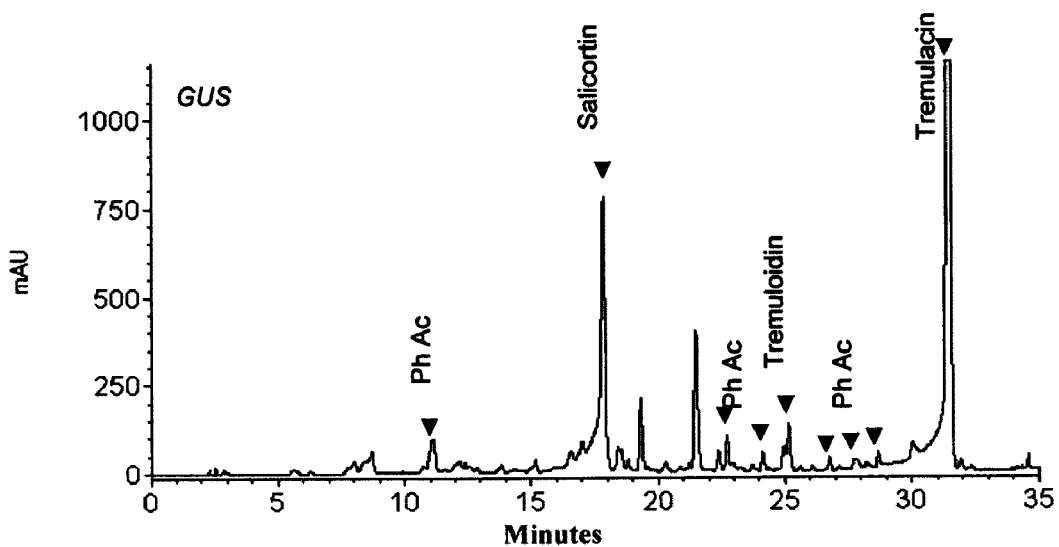
FIG. 6A is a graph illustrating an HPLC analysis of leaf tissue from transgenic P. tremula×tremuloides.
Figure 6B:
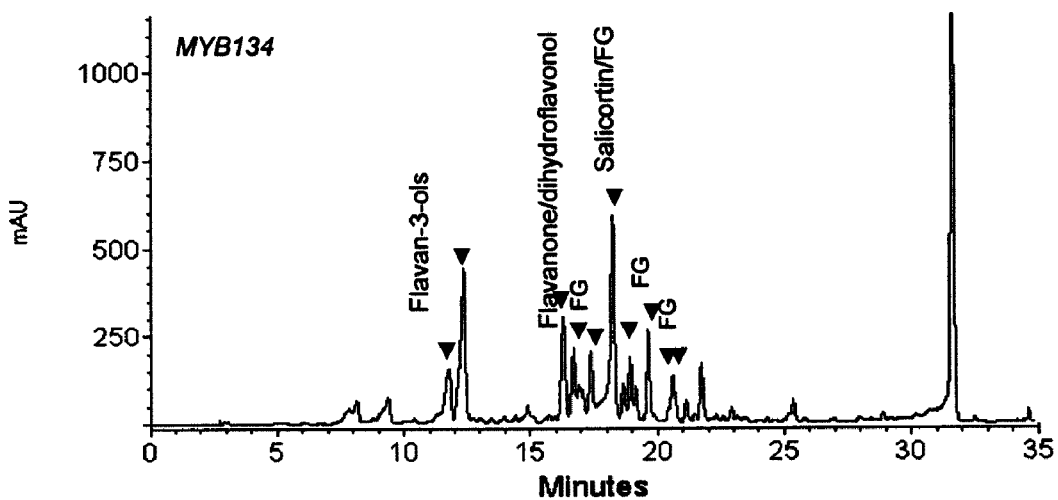
FIG. 6B is a graph illustrating an HPLC analysis of leaf tissue from transgenic P. tremula×tremuloides.

HPLC analysis of P. tremulaxtremuloides leaf tissue demonstrated that MYB134 overexpression caused other alterations to phenolic metabolism in addition to the large increase in PA concentrations. HPLC-DAD analysis of non-PA soluble phenolics in leaf extracts of a control 353-38 GUS (FIG. 6A) and in leaf extracts of an MYB134 overexpressor (FIG. 6B) show a reduction in PG concentration in the overexpressor on comparison to the control. FIG. 6 illustrates a representative Max-Plot chromatograms showing each peak at its $\lambda_{max}$. The reduction in PG concentrations dropped from 46.7±12.2 mg/g to 17.0±11.9 mg g$^{-1}$ fresh weight (FW). Levels of individual PGs (salicortin, tremuloidin, and tremulacin) are also shown in FIG. 6.

Figure 7A:
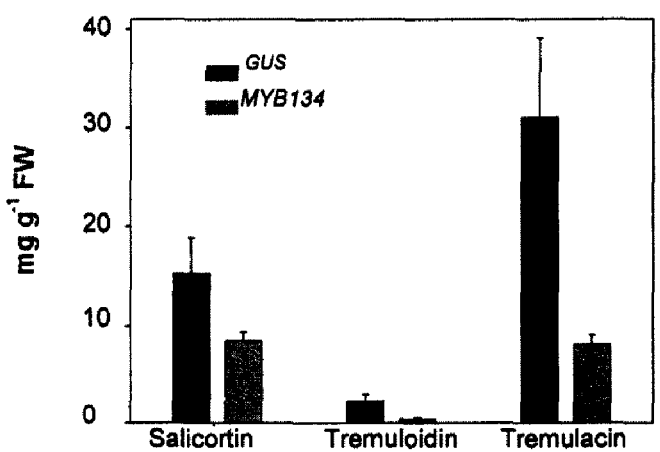
FIG. 7A is a bar graph illustrating phenolic glycoside concentrations in leaves of 353-38 GUS controls and MYB134 overexpressors.
Figure 7B:
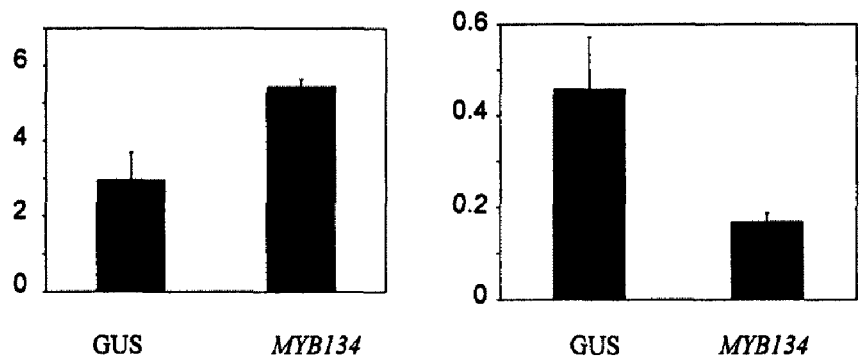
FIG. 7B is a bar graph illustrating the total phenolic acid and flavonol glycoside concentrations in leaves of 353-38 GUS controls and MYB134 overexpressors.

Increased concentrations of flavonol glycosides and decreased levels of non-flavonoid phenolic acids were also observed as illustrated in data extracted from the HPLC analysis of leaf tissue shown in FIGS. 7A and 7B. FIG. 7A illustrates phenolic glycoside (salicortin, tremuloidin, and tremulacin) concentrations in leaves of 353-38 GUS controls and MYB134 overexpressors. FIG. 7B illustrates total phenolic acid concentrations in the left panel and flavonol glycoside concentrations in the right panel, in leaves of 353-38 GUS controls and MYB134 overexpressors. For each of the figures, the data plotted is the mean of four independently transformed lines (GUS lines 1-4 and MYB134 overexpressor lines 2-5), having error bars indicating the SE of mean. Asterisks indicate significant differences using Student's t test (* P<0.05,  P<0.01, * P<0.001).

Anthocyanins were not detected in either control or transgenic leaves. A number of peaks corresponding to PA biosynthetic intermediates, including putative flavan-3-ols (catechin and epicatechin) and a flavanone/dihydroflavonol, were observed in MYB134 overexpressing leaf extracts but were undetectable in control leaves as shown in FIG. 6. The same pattern of reduced non-flavonoid phenylpropanoid compounds, and a moderate increase in non-PA flavonoids was also found in the high PA *P. tremula×alba* MYB134 overexpressing lines. A comparison of PA levels in four high MYB134 transgene expressing lines showed a significant increase in PA concentrations in all tissues analyzed (FIG. 7B). Overall, the increases in PA and flavonoid levels and the decrease in PG and phenolic acid levels resulted in a net increase in total soluble phenolics. Table 5 indicates the percent increase in total soluble phenolics in tissues of high PA-accumulating 353-38 MYB134 overexpressors relative to GUS control plants.

TABLE 5

| Tissue | % increase ± SE |
|---|---|
| leaves (LPI9-11)*** | 99.4 ± 10.2 |
| apical leaves** | 47.0 ± 8.6 |
| bark* | 71.7 ± 14.7 |
| wood* | 30.7 ± 4.9 |
| petioles*** | 54.9 ± 3.6 |
| young root* | 39.1 ± 12.2 |
| old root* | 68.2 ± 20.9 |

The total phenolics were assayed using the Folin-Ciocalteau assay (Singleton and Rossi, 1965). Error bars are SE of mean, n = 6.
Asterisks indicate significant difference between MYB134 overexpressors and controls using Student's t test (*P < 0.05, P < 0.01, *P < 0.001).

Of the eight independently transformed *P. tremula×tremuloides* MYB134 overexpressing lines that were analyzed shown in FIG. 5A, one exhibited a much lower increase in PA levels, line 1 of the P. txt MYB134 (clone INRA 353-38). Southern blot analysis using a probe complimentary to the neomycin phospho-transferase II gene present on the T-DNA demonstrated that this line exhibiting a lower PA level also contained about 5-6 T-DNA insertions, while all other lines contained only 1-2 T-DNA insertions. Northern analysis revealed a correspondingly lower level of transgene expression in this low expressing PA line as shown in FIG. 5B. The positive correlation between the level of MYB134 transgene expression and PA accumulation in this line supports that MYB134 is a regulator of the PA pathway.

Example 4

Forest Tent Caterpillar (FTC) Bioassays

In order to analyze the contrasting increases and decreases in PA and PG concentrations, the feeding preference and performance of an important insect herbivore of *P. tremuloides*, the forest tent caterpillar (FTC, *Malacosoma disstria* larvae) was assessed.

A series of bioassays using FTCs and leaf disks from a control (GUS) or MYB134 overexpressing plants were conducted. Three independent "choice" bioassays were conducted to determine whether early instar FTC would exhibit a feeding preference, and three independent "no-choice" experiments were run to determine whether or not larval survival would be affected by high PA/low PG foliage.

Figure 8:
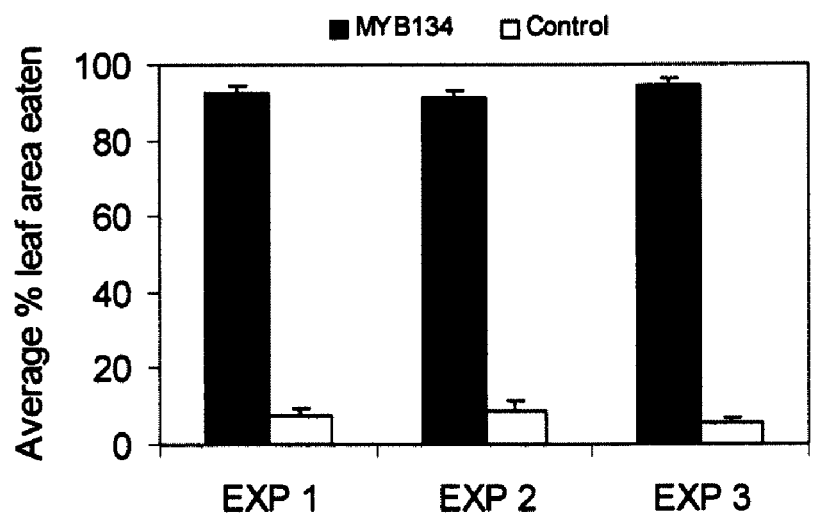
FIG. 8 is a chart illustrating feeding preferences of Forest Tent Caterpillars (FTC)

For choice experiments, FTC were placed in Petri dishes containing leaf disks from MYB134 overexpressing or control *P. tremula×tremuloides* (INRA 353-38). When given the choice, FTC exhibited a strong preference for the MYB134 overexpressing (high PA/low PG) leaf material in all three replications as shown in FIG. 8.

In the no-choice assays, FTC was placed on mature foliage that is a poor food source, resulting in a high mortality rate on the control tissue. Larvae was placed in Petri plates containing disks from equivalent leaves of either MYB134 or control (GUS) *P. tremula×tremuloides* (INRA 353-38) leaves. Larvae placed on leaf disks from the MYB134 overexpressing plants exhibited a significantly (P<0.01) lower mortality by day 8 in three independent experiments.

Example 5

Transformation of Forage Crops

In one exemplary embodiment *Medicago sativum* (Alfalfa) is transformed with at least one MYB transcription factor or fragment, more specifically, one of MYB134, MYB097 or MYB183 using methods known in the art, to enhance the expression of the flavonoid and PA pathway and increase PA accumulation in alfalfa.

Typically, alfalfa is a key component in feed for livestock. The presence of transformed alfalfa in fodder provides a method to modulate the microbial activity in ruminants using PAs. The presence of PA in a specific concentration range in feed prevents microbially-generated foaming in livestock, which is known to lead to bloat, and prevents the intake of large volumes of PAs by livestock, which leads to reduced nutrient uptake by ruminants.

Similarly, other forage crops known to those skilled in the art may also be transformed with at least one MYB transcription factor or fragment, more specifically, one of MYB134, MYB097 or MYB183 using methods known in the art. Examples of forage crops are sweet clover (genus *Trifolium*), red clover (*Trifolium pretense*), Alsike clover (*T. hybridum*), corn, wheat, barley, oats, raw silage, alfalfa, sorghums, and grass legume mix.

In a further embodiment, transformation of a forage crop with at least one MYB transcription factor or fragment, more specifically, one of MYB134, MYB097 or MYB183 using methods known in the art, increases expression of the flavonoid and PA pathway and in turn increases PA accumulation in those crops. Increased and over-expression of MYB transcription factors and fragments that correspond to an increase in PA expression further correspond to an increase PA synthesis in both the above and below ground forage crop components. It is known in the art that PA content in forage crops impacts for example, cows tolerance to worms, lambing percentages, lamb wool growth, and disease resistance in ruminants. Therefore, persons skilled in the art would understand that use MYB transcription factors and fragments to indirectly regulate and increase tannin synthesis would enable increased cows tolerance to worms, increased lambing percentages, increased lamb wool growth, and increased disease resistance in ruminants.

Example 6

Bloat Bioassays

Another exemplary embodiment relates to decreasing bloat related gas production. In vitro ruminal gas production may be quantified using ruminal fluid mixed with artificial saliva and minced alfalfa forage having an increased PA concentration. Bloat-related gas production is measured by plunger displacement using methods known in to those skilled in the art.

To conduct in vitro bloat assays, transgenic foliage having increased PA levels is fed to cattle for a period of several weeks. Cows are monitored visually for bloat using the Paisley and Horn scale. Cows that are identified as having reduced bloat in turn exhibit a decrease in methane emissions.

Example 7

Transformation of Fruit

In one exemplary embodiment an Apple is transformed with at least one MYB transcription factor or fragment, more specifically, one of MYB134, MYB097 or MYB183 using methods known in the art, to enhance the expression of the PA pathway and PA accumulation in leaves. Persons skilled in the art would understand that other fruits may also be transformed using similar methods.

More specifically Apple transformation is performed under the control of general or fruit-specific promoters using established *Agrobacterium*-based methods known in the art. The flesh of the apple and apple peel exhibits increased levels of PAs. High PA containing fruit have superior health-promoting properties when consumed in the diet, and enable greater resistance to microbial attack.

In a further embodiment fruit having increase PA levels may be cooked and dried fruit while retaining the high PA level. For example, transformed apple fruit may be dried, packaged and marketed as a health food product or food snack.

Example 11

Effects of MYB183 and MYB097 Overexpression in Poplar on Phenolic Metabolism and Gene Expression The role of MYB183 and MYB097 in the regulation of stress-induced PA metabolism was evaluated. To access the impact of these genes on phenolic metabolism MYB183 and MYB097 are overexpressed in poplar under the control of a double cauliflower mosaic virus (CaMV) 35S promoter. β-glucuronidase (GUS) overexpressing lines are produced as controls. Two genotypes, *P. tremula×tremuloides* (clone INRA 353-38) and *P. tremula×alba* (clone INRA 717-1-B4), are selected to examine MYB183 and MYB097 function because of the differences they exhibit in wound-induced PA metabolism. The *P. tremula×tremuloides* clone responded to mechanical wounding with transcriptional activation of the PA biosynthetic pathway, while this response was not observed in the. *tremula×alba* clone. Both clones are characterized by very low leaf PA levels under greenhouse conditions. MYB183 and MYB097 overexpressing poplar plants do not exhibit any obvious phenotypic differences when grown under greenhouse conditions.

The above-described embodiments have been provided as examples, for clarity in understanding the invention. A person of skill in the art will recognize that alterations, modifications and variations may be effected to the embodiments described above while remaining within the scope of the invention as defined by the claims appended hereto.

The invention claimed is:

1. An isolated nucleic acid molecule comprising a nucleotide sequence operably linked to a heterologous promoter, wherein said nucleotide sequence encodes a polypeptide having the amino acid sequence as set forth in SEQ ID NO: 26 and wherein expression of said polypeptide in a plant increases proanthocyanidin levels in the plant as compared to a plant of the same species lacking said nucleic acid molecule.

2. The isolated nucleic acid molecule according to claim 1, wherein said nucleotide sequence has at least 85% sequence identity to the nucleic acid sequence as set forth in SEQ ID NO: 11.

3. The isolated nucleic acid molecule according to claim 1, wherein said nucleotide sequence has at least 90% sequence identity to the nucleic acid sequence as set forth in SEQ ID NO: 11.

4. The isolated nucleic acid molecule according to claim 1, wherein said nucleotide sequence comprises the nucleic acid sequence as set forth in SEQ ID NO: 11.

5. A method of producing a transformed plant, wherein the method comprises transforming a plant cell with an isolated nucleic acid molecule comprising a nucleotide sequence encoding a polypeptide having the amino acid sequence of SEQ ID NO: 26, expressing said polypeptide in the plant cell and regenerating a transformed plant from the transformed cell.

6. The method of claim 5, wherein said nucleotide sequence has at least 85% sequence identity to the nucleic acid sequence as set forth in SEQ ID NO: 11.

7. The method of claim 5, wherein said nucleotide sequence has at least 90% sequence identity to the nucleic acid sequence as set forth in SEQ ID NO: 11.

8. The method of claim 5, wherein said nucleotide sequence comprises the nucleic acid sequence as set forth in SEQ ID NO: 11.

9. A plant cell transformed with the nucleic acid molecule of claim 1.

10. The plant cell according to claim 9, wherein said plant cell has an increased proanthocyanidin level as compared to an untransformed plant cell of the same species.

11. The plant cell according to claim 9, wherein said plant cell is regenerated into a plant, and wherein the plant comprises said nucleic acid molecule.

12. The plant cell according to claim 11, wherein said plant is selected from the group consisting of sweet clover, red clover, Alsike clover, corn, wheat, barley, oat, alfalfa, and sorghum.

13. A transformed plant transformed with the nucleic acid molecule of claim 1.

14. The transformed plant according to claim 13, wherein said transformed plant is a forage plant.

15. The transformed plant according to claim 14, wherein said forage plant is selected from the group consisting of sweet clover, red clover, Alsike clover, corn, wheat, barley, oat, alfalfa, and sorghum.

* * * * *

UNITED STATES PATENT AND TRADEMARK OFFICE
CERTIFICATE OF CORRECTION

PATENT NO. : 7,868,226 B2
APPLICATION NO. : 12/626844
DATED : January 11, 2011
INVENTOR(S) : Constabel and Mellway Page 1 of 1

It is certified that error appears in the above-identified patent and that said Letters Patent is hereby corrected as shown below:

In the Figures:
Delete Fig. 3A, and replace with the following:

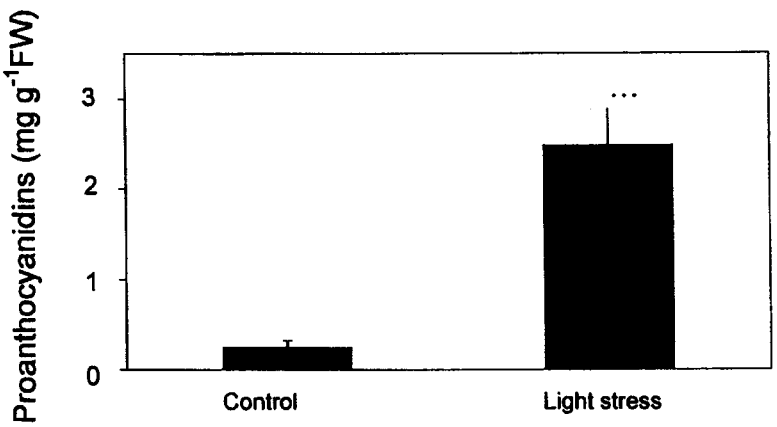

Fig. 3A

--                                                                                                          --.

In the Specification:

Column 4, line 30, delete "stress;" after "method;".

Column 7, line 54, "for" should be --for example--.

Column 12, line 29, "Torn" should be --Torr.--.

Column 12, line 63, "interne" should be --internet--.

Column 16, line 40, "15 µL," should be "15 µL".

Column 23, line 1, "11.9" should be --1.9--.

Signed and Sealed this
Twenty-third Day of August, 2011

David J. Kappos
*Director of the United States Patent and Trademark Office*

SEQUENCE LISTING

```
<160> NUMBER OF SEQ ID NOS: 27

<210> SEQ ID NO 1
<211> LENGTH: 1136
<212> TYPE: DNA
<213> ORGANISM: Populus tremuloides

<400> SEQUENCE: 1
cggccgttga gcttttgagg aatatagagg gagaatagag agaggatggg tagaagttca      60
aaaggggggc taattcgagg aacttggact gctactgaag acaaaattct tacagcatat     120
gttagaaaat atggtgaagg gaactgggct agggttacaa gggaaacagg tctgaagaga     180
tgtggcaaga gttgcaggct tcgttggctg aattatctaa aaccagatgt taaaagagga     240
aacattagcc cagatgaaga agatctcatt attaggcttc acaagctctt aggcaacaga     300
tgggctttaa tagctggaag gcttccaggt cggacggaca atgagatcaa gaattactgg     360
aattcaacct tgaaaagaaa ggtacaagct aacgatcaaa aacagcctag aagagggaat     420
aaagacacaa aaaaacaaac cagaaagacc tcaacaggat tgaatatggc ggcaccatgc     480
```

```
acaaacagta gtcttccttc accaccagtc ttagctgaaa atatagagac tgatcagatc    540
ctcacagcat cctccattga agaaggaacc ttggaaaaat atctgataga aaatcccaac    600
tcaaatgatg agctcttgct atttactaac gataatgatg tgccttgcaa cttcttgatg    660
gatcttgata tggggcagat gagcttctct gattttctcc aaactgatat cttctcagat    720
agcaataaca tgcttgttaa tgggcctgca ccttcttatc cagatgaagc ttctttgttc    780
cccgagaata tgctgcagaa ttggatgtgt gaggatggct tgaacttga actggctatg     840 ggtccttgat caacgatcac tgctttcgtt cttgtcaatt caaggcgatt aataagcatg    900
tcttctgctt cttcttcttc ttctccttct tcttcttctt ctttatcatt atcctttctt    960
gttccaggtt attgagatta ataaggggga gcagagttcg ctcatatatt ccctttgcct    1020
gtttccattt ttctcagcat ttgaacataa gaattccaat tagaaccgcg gtaagttgga    1080
tggtccctgt atggaagaaa cggcatgctt ttaattggaa cacaaatatc caatct        1136
```

<210> SEQ ID NO 2
<211> LENGTH: 887
<212> TYPE: DNA
<213> ORGANISM: Populus tremuloides

<400> SEQUENCE: 2

```
atgggaagga gtccatgttg ctccaaggaa ggactcaaca ggggagcctg gactgccttg     60
gaagacaaaa tactgatggc ttatattaaa gcccatggag aaggcaactg gagaaacctc    120
cccgagagag caggttttgaa gagatgtgga aagagctgta gactcagatg gttaaattat    180
cttagaccag acatcaagag aggcaacatt tcccatgatg aagaagaact cattatcagg    240
ctccataacc ttcttggtaa cagatggtcc ctaatagctg gaaggctacc tgggcgaaca    300
gacaatgaaa tcaagaatta ttggaacact actctgggga aaaagctaa aggccaatca     360 tcttcacaat ccaaacaaag ctctcaaaga aaatctagag caattaaacc catgaccagc    420
acccaaccat caaagtcaac acagacaacc caagtaatcc gcaccaaggc cactaggtgc    480
accaaggttt tgctctcatt acagtccacca ccaccgacac tgacaccact accaccacct   540
gaaattctct cctcaacagc catgaacgac ccctctcaag cttccttgat aaatcatcaa    600
caagatggtc caaattttca ttgcggaact gaagaggttc atgcatgtca tgatggctca    660
gatttcttca atttcgggaa gtggaatgaa attcaaccaa atgatatagaa cggagacaca    720 ctaatgaaga gtggttgtaa ccggaatttg tccagggggtt ctgaatattc cttgggctta   780
tttgatgacc tcatgttcaa ggactgggca ctgaatcatt gtcctgaaga caatgcaact    840
ttggacctag agtctctcgc acatttgctt gattctgaag agtggcc                  887
```

<210> SEQ ID NO 3
<211> LENGTH: 870
<212> TYPE: DNA
<213> ORGANISM: Populus tremuloides

<400> SEQUENCE: 3

```
atggggagga gtccatgttg ctccaaggag gggctcaaca gaggagcctg gactgcctta     60
gaagacaaaa tactgacggc gtatatcaag gcccacggag aaggcaaatg gagaaacctc    120
cccaagagag caggttttgaa gagatgtgga aagagctgta gactcagatg gttaaattat    180
cttagaccgg acatcaagag aggcaacatt tccaatgatg aagaagaact cattgtcagg    240
ctccataagc ttcttggtaa cagatggtct ttaatagctg gaaggctacc tgggcgaaca    300
gacaatgaaa tcaagaacta ctggaacact actctgggga agaaagcaac tgctcaagca    360
```

```
tctccacagt ccaaacaaaa ttcccagagc tttaaaaaac gagcaattga acccatgact    420
aacacccaat catcaaagtc aacactggca acccaagtaa tccccaccaa ggccactagg    480
tgcactaagg ttttcctctc attacagtca ccaccaccac caataccgcc acctaaaact    540
ctctcctcaa cagccataga cgacccacca caagctccct tgttaaatca tcaacaagat    600
agcccaaatc ttcactgtcg tgatgatgac tcagatttct tgaattttgg acactggaat    660
gagtttcaac cgagtgatgg aggtacacta attgacaatg attgtgacaa gaatctgtcc    720
attgattctt accattcctt agccgtatct gatgacctaa tgttcaagga ttgggccctg    780
aatcgttgtc tcgatgacaa ttcaactttg gacttggaat ctttggcaca tttgcttgac    840
tctgaagagt ggcctgagat gcgacattga                                     870
```

<210> SEQ ID NO 4
<211> LENGTH: 1093
<212> TYPE: DNA
<213> ORGANISM: Populus tremuloides

<400> SEQUENCE: 4

```
gtaccaagta tccagtcatc cagaggacat cgagtagcta gtagtgagat acagcaagag     60
atgggaagaa agccgaggtg ctcagcggat ggtatgaaca aaggagcatg gacacctctt    120
gaagatgaaa tgcttgtgga ttatgtcaag atscatggtg aaggtaaatg gagcaatatt    180
gtcaaagaaa caggacttaa gagatgtggg aagagttgca ggcttcgctg gatgaattat    240
ctgagacctg atattaagag aggcaacatc tcagatgatg aagaagacct cattatcagg    300
ctgcataagc tcttaggcaa cagatggtct ctgatagcag acggcttcc  gggacgaaca    360 gataacgaaa taaagaatta ttggcacacc aatatcgcta agaaggcaca acattcgcaa    420
tctcggaagc agcctrgagt tgataggaaa caaatagcat caggatctga aaatggggca    480
rcagcatcaa atktcaagaa tcagaccatt gaatcacagt actgcactac tggggtggtt    540
gttcccwcta ctgcattaca agaaaacaat atggctcaag atcatctagt tagtactctt    600
gcaatggcac catccaacac acatcatgaa atgaatcat  caagcaaggg gttagcatct    660
ggggataatg acaatttgtc caacattttg atggattttc attatatgga agacttctwc    720
aagattcttg attcagactt cccaaagtta agtgacctca atgatataac tagtactgct    780
aatcattcca mtaataccat acaggtagat ggtgatcatt atagtgtgtc tattaatgga    840
tgcaatccaa gagaaatagc agggttttct gaattgttgg aggcagattg gactagcaat    900
aaatgcgttc aagctgaaca aggttttgat ttcatgtcat tgctttcatt tcttgattta    960
accgatgagt aatggacaga agatgcctta gccataatc  tacgtcaagt tgctttcatg   1020
tccacgcctt ccaggctaat agttctcgag tttgaacctc tctcatgtta aaaaaaaaa   1080 aaaaaaaaaa aaa                                                     1093
```

<210> SEQ ID NO 5
<211> LENGTH: 1055
<212> TYPE: DNA
<213> ORGANISM: Populus tremuloides

<400> SEQUENCE: 5

```
agagatggga aggagtccat gttgctccaa ggaaggactc aacagggag  cctggactgc     60 cttggaagac aaaacactga tggcttatat taaagcccat ggagaaagca actggagaaa    120
cctccccgag agagcaggtt tgaagagatg tggtaagagc tgtagactca gatggttaaa    180
```

```
ttatcttaga ccagacatca agagaggcaa catttcccat gatgaagaag aactcattat      240
caggctccat aaccttcttg gtaacagatg gtccgtaata gctggaaggc tacctgggcg      300
gacagacaat gaaatcaaga attattggaa cactactctg gggaaaaaag ctaaaggcga      360
atcatcttca caatccaaac aaagctgtca agcaaatct agagcaatta aacccatgac       420
cagcacccaa ccatcaaagt caacacagac aacccaagta atccgcatca aggccactag      480
gtgcaccaag gttttgctct cattacagtc accaccaccg acacgacac cactaccacc       540 acctgaaatt ctctcctcaa cagccatgaa cgacccctct caagcttcct tgataaatca      600
tcaacaagat ggtccaaatt ttcattgcgg aactgaagag gttcatgcat gtcatgatgg      660
ctcagatttc ttcaatttcg ggaagtggaa tgaaattcaa ccaaatgata tagacggaga     720
tacactaatg aagagtggtt gtaaccggaa tttgtccagg ggttctgaat gttccttggg      780
catatttgat gacctcatgt tcaaggactg ggcactgaat cattgtcctg aagacaatgc      840
aactttggac ctagagtctc tcgcacattt gcttgattct gaagagtggc catgagatta      900
gacactgacg agaaactaca gcaaaatctc caccctagaa gatatattgg cacttgtggc      960
atatctcaat tgattattat tcgtagaaat caaagtaata attagcttgt gtatggtgtg     1020
aaattagagc aagtctgtaa tgatttagca tttgt                                 1055
```

```
<210> SEQ ID NO 6
<211> LENGTH: 355
<212> TYPE: DNA
<213> ORGANISM: Populus tremuloides

<400> SEQUENCE: 6
```

```
atggggagga gtccatgttg ctccaaggag gggctcaaca gaggagcctg gactgcctta       60
gaagacaaaa tactgacggc gtatatcaag gcccacggag aaggcaaatg gagaaacctc      120
cccaagagag caggtttgaa gagatgyggc aagagctgta gactcagatg gttaaattat      180
cttagaccgg acatcaagag aggcaacatt tccaatgatg aagaagaact cattgtcagg      240
ctccataagc ttcttggtaa cagatggtct ttaatagctg gaaggctacc tgggcgaaca      300
gacaatgaaa tcaagaacta ctggaacact actctgggga agaaagcaac tgctc           355
```

```
<210> SEQ ID NO 7
<211> LENGTH: 22
<212> TYPE: DNA
<213> ORGANISM: Populus tremuloides

<400> SEQUENCE: 7
```

```
ccatggggag gagtccatgt tg                                                22
```

```
<210> SEQ ID NO 8
<211> LENGTH: 26
<212> TYPE: DNA
<213> ORGANISM: Populus tremuloides

<400> SEQUENCE: 8
```

```
tctagatcat ggccactctt cagaat                                            26
```

```
<210> SEQ ID NO 9
<211> LENGTH: 19
<212> TYPE: DNA
<213> ORGANISM: Populus tremuloides

<400> SEQUENCE: 9
```

```
aaagctctca agaaaaatc                                                    19
```

<210> SEQ ID NO 10
<211> LENGTH: 19
<212> TYPE: DNA
<213> ORGANISM: Populus tremuloides

<400> SEQUENCE: 10
gtctccgtct atatcattt                                                    19

<210> SEQ ID NO 11
<211> LENGTH: 1040
<212> TYPE: DNA
<213> ORGANISM: Populus trichocarpa

<400> SEQUENCE: 11
gttgtggaag tgcgcgtgtg tggtgatcgt agagagagat ggggaggagt ccatgttgct        60
ccaaggaggg actcaacaga ggagcctgga ctgccttaga agacaaaata ctgacggcgt      120
atatcaaggc ccacggagaa ggcaaatgga gaaacctccc aagagagca ggtttgaaga       180 gatgcggcaa gagctgtaga ctcagatggt taaattatct tagaccggac atcaagagag      240
gcaacatttc caatgatgaa gaagaactca ttgtcaggct ccataagctt cttggaaaca      300
gatggtcttt aatagctgga aggctacctg ggcgaacaga caatgaaatc aagaactact      360
ggaacactac tctggggaag aaagccactg ctcaagcatc tccacagtcc aaacaaaatt      420
cccagagctt taaaaaacga gcaattgaac ccatgactaa cacccaatca tcaaagtcaa      480
cactggcaac ccaagtaatc cccaccaagg ccactaggtg cactaaggtt ttcctctcat      540
tacagtcccc accaccacca atactgccac ctaaaactct ctcctcaaca gccatagacg      600
acccaccaca agctcccttg ttaaatcatc aacaagatag cccaaatctt cacggccatg      660
atgactcaga tttcttgaat tttggacact ggaatgagtt tcaatcgagt gatggaggta      720
cactaattga caatgattgt gacaagaatc tgtccattga ttcttaccat tccttagcct      780
tatctgatga cctaatgttc aaggattggg ccctgaatcg ttgtctcgat gacaattcaa      840
ctttggactt ggaatctttg gcacatttgc ttgactctga agagtggcct gagatgcgac      900
attgacgaga aacgacgaca aaatctccac cgtagaagat atgtatacaa ttgatctgcc      960
catgaataaa taggcattca gtgttgatga tcaccacttg tagaatgtct taattgacta     1020
ttaatgtaga aatgaaagta                                                  1040

<210> SEQ ID NO 12
<211> LENGTH: 267
<212> TYPE: PRT
<213> ORGANISM: Populus tremuloides

<400> SEQUENCE: 12

Met Gly Arg Ser Ser Lys Gly Gly Leu Ile Arg Gly Thr Trp Thr Ala
1               5                   10                  15

Thr Glu Asp Lys Ile Leu Thr Ala Tyr Val Arg Lys Tyr Gly Glu Gly
                20                  25                  30

Asn Trp Ala Arg Val Thr Arg Glu Thr Gly Leu Lys Arg Cys Gly Lys
            35                  40                  45

Ser Cys Arg Leu Arg Trp Leu Asn Tyr Leu Lys Pro Asp Val Lys Arg
        50                  55                  60

Gly Asn Ile Ser Pro Asp Glu Glu Asp Leu Ile Ile Arg Leu His Lys
65                  70                  75                  80

Leu Leu Gly Asn Arg Trp Ala Leu Ile Ala Gly Arg Leu Pro Gly Arg

-continued

```
                85                  90                  95
Thr Asp Asn Glu Ile Lys Asn Tyr Trp Asn Ser Thr Leu Lys Arg Lys
            100                 105                 110

Val Gln Ala Asn Asp Gln Lys Gln Pro Arg Arg Gly Asn Lys Asp Thr
        115                 120                 125

Lys Lys Gln Thr Arg Lys Thr Ser Thr Gly Leu Asn Met Ala Ala Pro
    130                 135                 140

Cys Thr Asn Ser Ser Leu Pro Ser Pro Val Leu Ala Glu Asn Ile
145                 150                 155                 160

Glu Thr Asp Gln Ile Leu Thr Ala Ser Ser Ile Glu Glu Gly Thr Leu
                165                 170                 175

Glu Lys Tyr Leu Ile Glu Asn Pro Asn Ser Asn Asp Glu Leu Leu Leu
            180                 185                 190

Phe Thr Asn Asp Asn Asp Val Pro Cys Asn Phe Leu Met Asp Leu Asp
        195                 200                 205

Met Gly Gln Met Ser Phe Ser Asp Phe Leu Gln Thr Asp Ile Phe Ser
    210                 215                 220

Asp Ser Asn Asn Met Leu Val Asn Gly Pro Ala Pro Ser Tyr Pro Asp
225                 230                 235                 240

Glu Ala Ser Leu Phe Pro Glu Asn Met Leu Gln Asn Trp Met Cys Glu
                245                 250                 255

Asp Gly Phe Glu Leu Glu Leu Ala Met Gly Pro
            260                 265

<210> SEQ ID NO 13
<211> LENGTH: 296
<212> TYPE: PRT
<213> ORGANISM: Populus tremuloides

<400> SEQUENCE: 13

Met Gly Arg Ser Pro Cys Cys Ser Lys Glu Gly Leu Asn Arg Gly Ala
1               5                   10                  15

Trp Thr Ala Leu Glu Asp Lys Ile Leu Met Ala Tyr Ile Lys Ala His
            20                  25                  30

Gly Glu Gly Asn Trp Arg Asn Leu Pro Glu Arg Ala Gly Leu Lys Arg
        35                  40                  45

Cys Gly Lys Ser Cys Arg Leu Arg Trp Leu Asn Tyr Leu Arg Pro Asp
    50                  55                  60

Ile Lys Arg Gly Asn Ile Ser His Asp Glu Glu Leu Ile Ile Arg
65                  70                  75                  80

Leu His Asn Leu Leu Gly Asn Arg Trp Ser Leu Ile Ala Gly Arg Leu
                85                  90                  95

Pro Gly Arg Thr Asp Asn Glu Ile Lys Asn Tyr Trp Asn Thr Thr Leu
            100                 105                 110

Gly Lys Lys Ala Lys Gly Gln Ser Ser Gln Ser Lys Gln Ser Ser
        115                 120                 125

Gln Arg Lys Ser Arg Ala Ile Lys Pro Met Thr Ser Thr Gln Pro Ser
    130                 135                 140

Lys Ser Thr Gln Thr Gln Val Ile Arg Thr Lys Ala Thr Arg Cys
145                 150                 155                 160

Thr Lys Val Leu Leu Ser Leu Gln Ser Pro Pro Thr Leu Thr Pro
                165                 170                 175

Leu Pro Pro Pro Glu Ile Leu Ser Ser Thr Ala Met Asn Asp Pro Ser
            180                 185                 190
```

```
Gln Ala Ser Leu Ile Asn His Gln Gln Asp Gly Pro Asn Phe His Cys
        195                 200                 205

Gly Thr Glu Glu Val His Ala Cys His Asp Gly Ser Asp Phe Phe Asn
    210                 215                 220

Phe Gly Lys Trp Asn Glu Ile Gln Pro Asn Asp Ile Asp Gly Asp Thr
225                 230                 235                 240

Leu Met Lys Ser Gly Cys Asn Arg Asn Leu Ser Arg Gly Ser Glu Tyr
                245                 250                 255

Ser Leu Gly Leu Phe Asp Asp Leu Met Phe Lys Asp Trp Ala Leu Asn
            260                 265                 270

His Cys Pro Glu Asp Asn Ala Thr Leu Asp Leu Glu Ser Leu Ala His
        275                 280                 285

Leu Leu Asp Ser Glu Glu Trp Pro
        290                 295

<210> SEQ ID NO 14
<211> LENGTH: 289
<212> TYPE: PRT
<213> ORGANISM: Populus tremuloides

<400> SEQUENCE: 14

Met Gly Arg Ser Pro Cys Cys Ser Lys Glu Gly Leu Asn Arg Gly Ala
1               5                   10                  15

Trp Thr Ala Leu Glu Asp Lys Ile Leu Thr Ala Tyr Ile Lys Ala His
            20                  25                  30

Gly Glu Gly Lys Trp Arg Asn Leu Pro Lys Arg Ala Gly Leu Lys Arg
        35                  40                  45

Cys Gly Lys Ser Cys Arg Leu Arg Trp Leu Asn Tyr Leu Arg Pro Asp
    50                  55                  60

Ile Lys Arg Gly Asn Ile Ser Asn Asp Glu Glu Leu Ile Val Arg
65                  70                  75                  80

Leu His Lys Leu Leu Gly Asn Arg Trp Ser Leu Ile Ala Gly Arg Leu
                85                  90                  95

Pro Gly Arg Thr Asp Asn Glu Ile Lys Asn Tyr Trp Asn Thr Thr Leu
            100                 105                 110

Gly Lys Lys Ala Thr Ala Gln Ala Ser Pro Gln Ser Lys Gln Asn Ser
        115                 120                 125

Gln Ser Phe Lys Lys Arg Ala Ile Glu Pro Met Thr Asn Thr Gln Ser
    130                 135                 140

Ser Lys Ser Thr Leu Ala Thr Gln Val Ile Pro Thr Lys Ala Thr Arg
145                 150                 155                 160

Cys Thr Lys Val Phe Leu Ser Leu Gln Ser Pro Pro Pro Ile Pro
                165                 170                 175

Pro Pro Lys Thr Leu Ser Ser Thr Ala Ile Asp Asp Pro Pro Gln Ala
            180                 185                 190

Pro Leu Leu Asn His Gln Gln Asp Ser Pro Asn Leu His Cys Arg Asp
        195                 200                 205

Asp Asp Ser Asp Phe Leu Asn Phe Gly His Trp Asn Glu Phe Gln Pro
    210                 215                 220

Ser Asp Gly Gly Thr Leu Ile Asp Asn Asp Cys Asp Lys Asn Leu Ser
225                 230                 235                 240

Ile Asp Ser Tyr His Ser Leu Ala Val Ser Asp Leu Met Phe Lys
                245                 250                 255

Asp Trp Ala Leu Asn Arg Cys Leu Asp Asp Asn Ser Thr Leu Asp Leu
            260                 265                 270
```

```
Glu Ser Leu Ala His Leu Leu Glu Ser Glu Glu Trp Pro Glu Met Arg
        275                 280                 285

His

<210> SEQ ID NO 15
<211> LENGTH: 303
<212> TYPE: PRT
<213> ORGANISM: Populus tremuloides
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (126)..(126)
<223> OTHER INFORMATION: Xaa can be any naturally occurring amino acid
<220> FEATURE:
<221> NAME/KEY: misc_feature
<222> LOCATION: (141)..(141)
<223> OTHER INFORMATION: Xaa can be any naturally occurring amino acid
<220> FEATURE:
<221> NAME/KEY: misc_feature
<222> LOCATION: (145)..(145)
<223> OTHER INFORMATION: Xaa can be any naturally occurring amino acid
<220> FEATURE:
<221> NAME/KEY: misc_feature
<222> LOCATION: (163)..(163)
<223> OTHER INFORMATION: Xaa can be any naturally occurring amino acid
<220> FEATURE:
<221> NAME/KEY: misc_feature
<222> LOCATION: (220)..(220)
<223> OTHER INFORMATION: Xaa can be any naturally occurring amino acid
<220> FEATURE:
<221> NAME/KEY: misc_feature
<222> LOCATION: (244)..(244)
<223> OTHER INFORMATION: Xaa can be any naturally occurring amino acid

<400> SEQUENCE: 15

Met Gly Arg Lys Pro Arg Cys Ser Ala Asp Gly Met Asn Lys Gly Ala
1               5                   10                  15

Trp Thr Pro Leu Glu Asp Glu Met Leu Val Asp Tyr Val Lys Xaa His
            20                  25                  30

Gly Glu Gly Lys Trp Ser Asn Ile Val Lys Glu Thr Gly Leu Lys Arg
        35                  40                  45

Cys Gly Lys Ser Cys Arg Leu Arg Trp Met Asn Tyr Leu Arg Pro Asp
    50                  55                  60

Ile Lys Arg Gly Asn Ile Ser Asp Asp Glu Asp Leu Ile Ile Arg
65                  70                  75                  80

Leu His Lys Leu Leu Gly Asn Arg Trp Ser Leu Ile Ala Gly Arg Leu
                85                  90                  95

Pro Gly Arg Thr Asp Asn Glu Ile Lys Asn Tyr Trp His Thr Asn Ile
            100                 105                 110

Ala Lys Lys Ala Gln His Ser Gln Ser Arg Lys Gln Pro Xaa Val Asp
        115                 120                 125

Arg Lys Gln Ile Ala Ser Gly Ser Glu Asn Gly Ala Xaa Ala Ser Asn
    130                 135                 140

Xaa Lys Asn Gln Thr Ile Glu Ser Gln Tyr Cys Thr Thr Gly Val Val
145                 150                 155                 160

Val Pro Xaa Thr Ala Leu Gln Glu Asn Asn Met Ala Gln Asp His Leu
                165                 170                 175

Val Ser Thr Leu Ala Met Ala Pro Ser Asn Thr His His Glu Asn Glu
            180                 185                 190

Ser Ser Ser Lys Gly Leu Ala Ser Gly Asp Asn Asp Asn Leu Ser Asn
```

```
                        195                 200                 205
Ile Leu Met Asp Phe His Tyr Met Glu Asp Phe Xaa Lys Ile Leu Asp
    210                 215                 220

Ser Asp Phe Pro Lys Leu Ser Asp Leu Asn Asp Ile Thr Ser Thr Ala
225                 230                 235                 240

Asn His Ser Xaa Asn Thr Ile Gln Val Asp Gly Asp His Tyr Ser Val
                245                 250                 255

Ser Ile Asn Gly Cys Asn Pro Arg Glu Ile Ala Gly Phe Ser Glu Leu
            260                 265                 270

Leu Glu Ala Asp Trp Thr Ser Asn Lys Cys Val Gln Ala Glu Gln Gly
        275                 280                 285

Phe Asp Phe Met Ser Leu Leu Ser Phe Leu Asp Leu Thr Asp Glu
    290                 295                 300

<210> SEQ ID NO 16
<211> LENGTH: 296
<212> TYPE: PRT
<213> ORGANISM: Populus tremuloides

<400> SEQUENCE: 16

Met Gly Arg Ser Pro Cys Cys Ser Lys Glu Gly Leu Asn Arg Gly Ala
1               5                   10                  15

Trp Thr Ala Leu Glu Asp Lys Thr Leu Met Ala Tyr Ile Lys Ala His
            20                  25                  30

Gly Glu Ser Asn Trp Arg Asn Leu Pro Glu Arg Ala Gly Leu Lys Arg
        35                  40                  45

Cys Gly Lys Ser Cys Arg Leu Arg Trp Leu Asn Tyr Leu Arg Pro Asp
    50                  55                  60

Ile Lys Arg Gly Asn Ile Ser His Asp Glu Glu Leu Ile Ile Arg
65                  70                  75                  80

Leu His Asn Leu Leu Gly Asn Arg Trp Ser Val Ile Ala Gly Arg Leu
                85                  90                  95

Pro Gly Arg Thr Asp Asn Glu Ile Lys Asn Tyr Trp Asn Thr Thr Leu
            100                 105                 110

Gly Lys Lys Ala Lys Gly Glu Ser Ser Gln Ser Lys Gln Ser Cys
        115                 120                 125

Gln Ser Lys Ser Arg Ala Ile Lys Pro Met Thr Ser Thr Gln Pro Ser
    130                 135                 140

Lys Ser Thr Gln Thr Thr Gln Val Ile Arg Ile Lys Ala Thr Arg Cys
145                 150                 155                 160

Thr Lys Val Leu Leu Ser Leu Gln Ser Pro Pro Thr Arg Thr Pro
                165                 170                 175

Leu Pro Pro Pro Glu Ile Leu Ser Ser Thr Ala Met Asn Asp Pro Ser
            180                 185                 190

Gln Ala Ser Leu Ile Asn His Gln Gln Asp Gly Pro Asn Phe His Cys
        195                 200                 205

Gly Thr Glu Glu Val His Ala Cys His Asp Gly Ser Asp Phe Phe Asn
    210                 215                 220

Phe Gly Lys Trp Asn Glu Ile Gln Pro Asn Asp Ile Asp Gly Asp Thr
225                 230                 235                 240

Leu Met Lys Ser Gly Cys Asn Arg Asn Leu Ser Arg Gly Ser Glu Cys
                245                 250                 255

Ser Leu Gly Ile Phe Asp Asp Leu Met Phe Lys Asp Trp Ala Leu Asn
            260                 265                 270
```

```
His Cys Pro Glu Asp Asn Ala Thr Leu Asp Leu Glu Ser Leu Ala His
        275                 280                 285

Leu Leu Asp Ser Glu Glu Trp Pro
    290                 295

<210> SEQ ID NO 17
<211> LENGTH: 103
<212> TYPE: PRT
<213> ORGANISM: Populus tremuloides

<400> SEQUENCE: 17

Leu Asn Arg Gly Ala Trp Thr Ala Leu Glu Asp Lys Ile Leu Thr Ala
1               5                   10                  15

Tyr Ile Lys Ala His Gly Glu Gly Lys Trp Arg Asn Leu Pro Lys Arg
            20                  25                  30

Ala Gly Leu Lys Arg Cys Gly Lys Ser Cys Arg Leu Arg Trp Leu Asn
        35                  40                  45

Tyr Leu Arg Pro Asp Ile Lys Arg Gly Asn Ile Ser Asn Asp Glu Glu
    50                  55                  60

Glu Leu Ile Val Arg Leu His Lys Leu Leu Gly Asn Arg Trp Ser Leu
65                  70                  75                  80

Ile Ala Gly Arg Leu Pro Gly Arg Thr Asp Asn Glu Ile Lys Asn Tyr
                85                  90                  95

Trp Asn Thr Thr Leu Gly Lys
            100

<210> SEQ ID NO 18
<211> LENGTH: 10
<212> TYPE: PRT
<213> ORGANISM: Populus tremuloides

<400> SEQUENCE: 18

Arg Gly Ala Trp Thr Ala Leu Glu Asp Lys
1               5                   10

<210> SEQ ID NO 19
<211> LENGTH: 10
<212> TYPE: PRT
<213> ORGANISM: Populus tremuloides

<400> SEQUENCE: 19

Lys Gly Ala Trp Thr Ala Leu Glu Asp Lys
1               5                   10

<210> SEQ ID NO 20
<211> LENGTH: 11
<212> TYPE: PRT
<213> ORGANISM: Populus tremuloides

<400> SEQUENCE: 20

Arg Gly Ala Trp Thr Ala Leu Glu Asp Lys Ile
1               5                   10

<210> SEQ ID NO 21
<211> LENGTH: 10
<212> TYPE: PRT
<213> ORGANISM: Populus tremuloides

<400> SEQUENCE: 21

Cys Gly Lys Ser Cys Arg Leu Arg Trp Leu
1               5                   10
```

```
<210> SEQ ID NO 22
<211> LENGTH: 10
<212> TYPE: PRT
<213> ORGANISM: Populus tremuloides

<400> SEQUENCE: 22

Cys Gly Lys Ser Cys Arg Ile Arg Trp Leu
1               5                   10

<210> SEQ ID NO 23
<211> LENGTH: 10
<212> TYPE: PRT
<213> ORGANISM: Populus tremuloides

<400> SEQUENCE: 23

Cys Gly Lys Ser Cys Arg Val Arg Trp Leu
1               5                   10

<210> SEQ ID NO 24
<211> LENGTH: 10
<212> TYPE: PRT
<213> ORGANISM: Populus tremuloides

<400> SEQUENCE: 24

Val Ile Pro Thr Lys Ala Thr Arg Cys Thr
1               5                   10

<210> SEQ ID NO 25
<211> LENGTH: 289
<212> TYPE: PRT
<213> ORGANISM: Populus tremuloides

<400> SEQUENCE: 25

Met Gly Arg Ser Pro Cys Cys Ser Lys Glu Gly Leu Asn Arg Gly Ala
1               5                   10                  15

Trp Thr Ala Leu Glu Asp Lys Ile Leu Thr Ala Tyr Ile Lys Ala His
                20                  25                  30

Gly Glu Gly Lys Trp Arg Asn Leu Pro Lys Arg Ala Gly Leu Lys Arg
            35                  40                  45

Cys Gly Lys Ser Cys Arg Leu Arg Trp Ile Asn Tyr Leu Arg Pro Asp
        50                  55                  60

Ile Lys Arg Gly Asn Ile Ser Asn Asp Glu Glu Leu Ile Val Arg
65                  70                  75                  80

Leu His Lys Leu Leu Gly Asn Arg Trp Ser Leu Ile Ala Gly Arg Leu
                85                  90                  95

Pro Gly Arg Thr Asp Asn Glu Ile Lys Asn Tyr Trp Asn Thr Thr Leu
            100                 105                 110

Gly Lys Lys Ala Thr Ala Gln Ala Ser Pro Gln Ser Lys Gln Asn Ser
        115                 120                 125

Gln Ser Phe Lys Lys Arg Ala Ile Glu Pro Met Thr Asn Thr Gln Ser
    130                 135                 140

Ser Lys Ser Thr Leu Ala Thr Gln Val Ile Pro Thr Lys Ala Thr Arg
145                 150                 155                 160

Cys Thr Lys Val Phe Leu Ser Leu Gln Ser Pro Pro Pro Ile Pro
                165                 170                 175

Pro Pro Lys Thr Leu Ser Ser Thr Ala Ile Asp Asp Pro Pro Gln Ala
            180                 185                 190

Pro Leu Leu Asn His Gln Gln Asp Ser Pro Asn Leu His Cys Arg Asp
        195                 200                 205
```

```
Asp Asp Ser Asp Phe Leu Asn Phe Gly His Trp Asn Glu Phe Gln Pro
        210                 215                 220

Ser Asp Gly Gly Thr Leu Ile Asp Asn Asp Cys Asp Lys Asn Leu Ser
225                 230                 235                 240

Ile Asp Ser Tyr His Ser Leu Ala Val Ser Asp Leu Met Phe Lys
                245                 250                 255

Asp Trp Ala Leu Asn Arg Cys Leu Asp Asp Asn Ser Thr Leu Asp Leu
        260                 265                 270

Glu Ser Leu Ala His Leu Leu Glu Ser Glu Glu Trp Pro Glu Met Arg
        275                 280                 285

His

<210> SEQ ID NO 26
<211> LENGTH: 288
<212> TYPE: PRT
<213> ORGANISM: Populus tremuloides

<400> SEQUENCE: 26

Met Gly Arg Ser Pro Cys Cys Ser Lys Glu Gly Leu Asn Arg Gly Ala
1               5                   10                  15

Trp Thr Ala Leu Glu Asp Lys Ile Leu Thr Ala Tyr Ile Lys Ala His
            20                  25                  30

Gly Glu Gly Lys Trp Arg Asn Leu Pro Lys Arg Ala Gly Leu Lys Arg
        35                  40                  45

Cys Gly Lys Ser Cys Arg Leu Arg Trp Leu Asn Tyr Leu Arg Pro Asp
50                  55                  60

Ile Lys Arg Gly Asn Ile Ser Asn Asp Glu Glu Leu Ile Val Arg
65                  70                  75                  80

Leu His Lys Leu Leu Gly Asn Arg Trp Ser Leu Ile Ala Gly Arg Leu
                85                  90                  95

Pro Gly Arg Thr Asp Asn Glu Ile Lys Asn Tyr Trp Asn Thr Thr Leu
            100                 105                 110

Gly Lys Lys Ala Thr Ala Gln Ala Ser Pro Gln Ser Lys Gln Asn Ser
        115                 120                 125

Gln Ser Phe Lys Lys Arg Ala Ile Glu Pro Met Thr Asn Thr Gln Ser
    130                 135                 140

Ser Lys Ser Thr Leu Ala Thr Gln Val Ile Pro Thr Lys Ala Thr Arg
145                 150                 155                 160

Cys Thr Lys Val Phe Leu Ser Leu Gln Ser Pro Pro Pro Ile Leu
                165                 170                 175

Pro Pro Lys Thr Leu Ser Ser Thr Ala Ile Asp Asp Pro Pro Gln Ala
            180                 185                 190

Pro Leu Leu Asn His Gln Gln Asp Ser Pro Asn Leu His Gly His Asp
        195                 200                 205

Asp Ser Asp Phe Leu Asn Phe Gly His Trp Asn Glu Phe Gln Ser Ser
    210                 215                 220

Asp Gly Gly Thr Leu Ile Asp Asn Asp Cys Asp Lys Asn Leu Ser Ile
225                 230                 235                 240

Asp Ser Tyr His Ser Leu Ala Leu Ser Asp Leu Met Phe Lys Asp
                245                 250                 255

Trp Ala Leu Asn Arg Cys Leu Asp Asp Asn Ser Thr Leu Asp Leu Glu
            260                 265                 270

Ser Leu Ala His Leu Leu Asp Ser Glu Glu Trp Pro Glu Met Arg His
        275                 280                 285
```

<210> SEQ ID NO 27
<211> LENGTH: 1149
<212> TYPE: DNA
<213> ORGANISM: Populus tremuloides

<400> SEQUENCE: 27

| | | | | | |
|---|---|---|---|---|---|
| atcatcccaa | tcgaatatat | tgcttgagct | tttgaggaat | atagagggag | aatagagaga | 60 |
| ggatgggtag | aagtycwama | ggggggmtaa | ttmgaggaac | ttggactgct | actgaagaca | 120 |
| aaattcttac | agcatatgtt | agaaattatg | gtgaagggaa | ctgggctagg | gttmcaargg | 180 |
| aaacaggtct | gaagagatgt | ggcaagagtt | gcaggcttcg | ttggctgaat | tatctaaaac | 240 |
| cagatgttaa | aagaggaaac | attrgcccag | atgaagaaga | tctcattatt | aggcttcaca | 300 |
| agctcttagg | caacagatgg | gctttaatag | ctggaaggmt | tccaggtcgg | acggacaatg | 360 |
| agatcaagaa | ttactggaat | tcaaccttga | aaagaaaggt | acaagctaac | gatcaaaaac | 420 |
| agcctagaag | agggaataaa | gacacwaaaa | aacaaaccag | aaagacctca | aywggattgr | 480 |
| atawggcggc | accatgcaca | aacagtagtc | ttccttcacc | accagtcttr | gmtgaaaata | 540 |
| yagagactga | tcagatyctc | acagcatcct | ccattgaaga | aggaaccttg | gaaaaaatat | 600 |
| ctgatagmaa | atcccaactc | aaatgatgag | ctcttgctat | tkactaacga | taatgatgtg | 660 |
| ccttgcaact | tcttgatgga | tcttgatatg | gggcagatga | gcttctctga | ttttctccaa | 720 |
| actgatatct | tctcagatag | caataacatg | cttgttaatg | ggcctgcacc | ttcttatcca | 780 |
| gatgaagctt | cttygttccc | cgaggctatg | ctgcagaatt | ggatatgtga | ggatggcttt | 840 |
| gracttgaac | tggctatggg | tccytgatca | acgatcactg | ctttctttct | tgtcaattca | 900 |
| aggcgattaa | taagcatgtc | ttctgcttct | tcttcttctt | tatcattatc | ctttcttgtt | 960 |
| ccaggttaty | gasattaaat | aaggggagca | gagttcgctc | atatatatat | tccctttgcc | 1020 |
| tgtttccatt | tttctcagca | tttgaacata | agaattccaa | ttagaataag | ttgratggtc | 1080 |
| cctgtatgga | agaaacggca | tgcttttaay | tggaacacaa | atatccaatc | taaaaaaaaa | 1140 |
| aaaaaaaaa | | | | | | 1149 |